United States Patent
Jansen-Dürr et al.

(10) Patent No.: US 9,249,212 B2
(45) Date of Patent: Feb. 2, 2016

(54) ANTI-HPV E7 ANTIBODIES

(75) Inventors: Pidder Jansen-Dürr, Innsbruck (AT); Werner Zwerschke, Innsbruck (AT); Haymo Pircher, Zirl (AT); Daniela Ehehalt, Innsbruck (AT); Barbara Lener, Innsbruck (AT); Kerstin Dreier, Innsbruck (AT)

(73) Assignees: OSTERREICHISCHE AKADEMIE DER WISSENCHAFTEN, Wien (AT); AUSTRIA WIRTSCHAFTSSERVICE GESELLSCHAFT MBH, Wien (AT)

( * ) Notice: Subject to any disclaimer, the term of this patent is extended or adjusted under 35 U.S.C. 154(b) by 255 days.

(21) Appl. No.: 13/578,985

(22) PCT Filed: Feb. 16, 2011

(86) PCT No.: PCT/EP2011/000728
§ 371 (c)(1),
(2), (4) Date: Aug. 14, 2012

(87) PCT Pub. No.: WO2011/101122
PCT Pub. Date: Aug. 25, 2011

(65) Prior Publication Data
US 2013/0029322 A1    Jan. 31, 2013

(30) Foreign Application Priority Data

Feb. 16, 2010 (EP) .................................... 10001569
Sep. 30, 2010 (EP) .................................... 10011978

(51) Int. Cl.
*C07K 16/08* (2006.01)
*G01N 33/569* (2006.01)

(52) U.S. Cl.
CPC ........ *C07K 16/084* (2013.01); *G01N 33/56983* (2013.01); *C07K 2317/33* (2013.01); *C07K 2317/34* (2013.01); *G01N 2333/025* (2013.01)

(58) Field of Classification Search
None
See application file for complete search history.

(56) References Cited

U.S. PATENT DOCUMENTS

| 7,026,443 | B1 * | 4/2006 | Sette et al. .................... 530/300 |
| 7,732,166 | B2 | 6/2010 | Cheng |
| 2007/0166699 | A1 | 7/2007 | Zwerschke et al. |
| 2008/0044809 | A1 | 2/2008 | Cheng |
| 2008/0199852 | A1 | 8/2008 | Cheng |
| 2010/0151444 | A1 | 6/2010 | Cheng |
| 2010/0167269 | A1 | 7/2010 | Cheng |

FOREIGN PATENT DOCUMENTS

| FR | 2794371 A1 | 12/2000 |
| WO | 2005/026731 A1 | 3/2005 |
| WO | 2006/085822 A1 | 8/2006 |
| WO | 2007/059492 A2 | 5/2007 |

OTHER PUBLICATIONS

Braspenning et al. The CXXC Zn binding motifs of the human papillomavirus type 16 E7 oncoprotein are not required for its in vitro transforming activity in rodent cells. Oncogene. Feb. 26, 1998;16(8):1085-9.*
Lidqvist, M. et al.: "Phage display for site-specific immunization and characterization of high-risk human papillomavirus specific E7 monoclonal antibodies", Journal of Immunological Methods, Elsevier Science Publishers B.V., Amsterdam. NL LNKD-DOI:10.1016/J.JIM.2008.06.002, vol. 337, No. 2, Sep. 15, 2008, pp. 88-96, XP023977062, ISSN: 0022-1759 [retrieved on Jul. 9, 2008].
Ressler, Sigrun et al.: "High-risk human papillomavirus E7 oncoprotein detection in cervical squamous cell carcinoma.", Clinical Cancer Research: An Official Journal of the American Association for Cancer Research Dec. 1, 2007 LNKD-PUBMED:18056184, vol. 13, No. 23, Dec. 1, 2007, pp. 7067-7072, XP002587786, ISSN: 1078-0432.
Fiedler, Marc et al: "Expression of the high-risk human papillomavirus type 18 and 45 E7 oncoproteins in cervical carcinoma biopsies", Journal of General Virology, vol. 86, no. Part 12, Dec. 2005 pp. 3235-3241, XP002587788, ISSN: 0022-1317.
Krchnak, V. et al: "Synthetic Peptides Derived From E7 Region of Human Papillomavirus Type 16 Used as Antigens in Elisa", Journal of General Virology, vol. 71, No. 11, 1990, pp. 2719-2724, XP002635493, ISSN: 0022-1317.
Suchankova, A. et al: "Comparison of Elisa and Western Blotting for Human Papillomavirus Type 16 E7 Antibody Determination", Journal of General Virology, vol. 72, No. 10, 1991, pp. 2577-2581, XP002635494, ISSN: 0022-1317.
Krchnak, V. et al: "Identification of Seroreactive Epitopes of Human Papillomavirus Type 18 E7 Protein by Synthetic Peptides", Acta Virologica, Academia Prague, Prague, CS, vol. 37, No. 5, Oct. 1, 1993, pp. 395-402, XP009050452, ISSN: 0001-723X, pp. 398,400-p. 401; figures 1, 2.
Nindl, I. et al: "Antibodies against linear and conformational epitopes of the human papillomavirus (HPV) type 16 E6 and E7 oncoproteins in sera of cervical cancer patients", Archives of Virology, Springer Wien, AT, Vol. 137, Jan. 1, 1994, pp. 341-353, XP002958776, ISSN: 0304-8608, DOI:10.1007/BF01309480.
Drier, K. et al: Subcellular localization of the human papillomavirus 16 E7 oncoprotein in CaSki cells and its detection in cervical adenocarcinoma and adenocarcinoma in situ:, Virology, Academic Press, Orlando, US, vol. 409, No. 1, Jan. 5, 2011, pp. 54-68, XP027524828, ISSN: 0042-6822, [retrieved on Nov. 24, 2010].
International Search Report and Written Opinion of the ISA, ISA/EP, Rijswijk, NL, mailed Jun. 29, 2011.

* cited by examiner

*Primary Examiner* — Michelle S Horning
(74) *Attorney, Agent, or Firm* — Harness, Dickey & Pierce, P.L.C.; Stephen T. Olson

(57) ABSTRACT

Monoclonal anti-HPV (human papillomavirus) E7 antibodies are capable of specifically recognizing an epitope of the C-terminal or the N-terminal region of a HPV E7 protein.

22 Claims, 21 Drawing Sheets

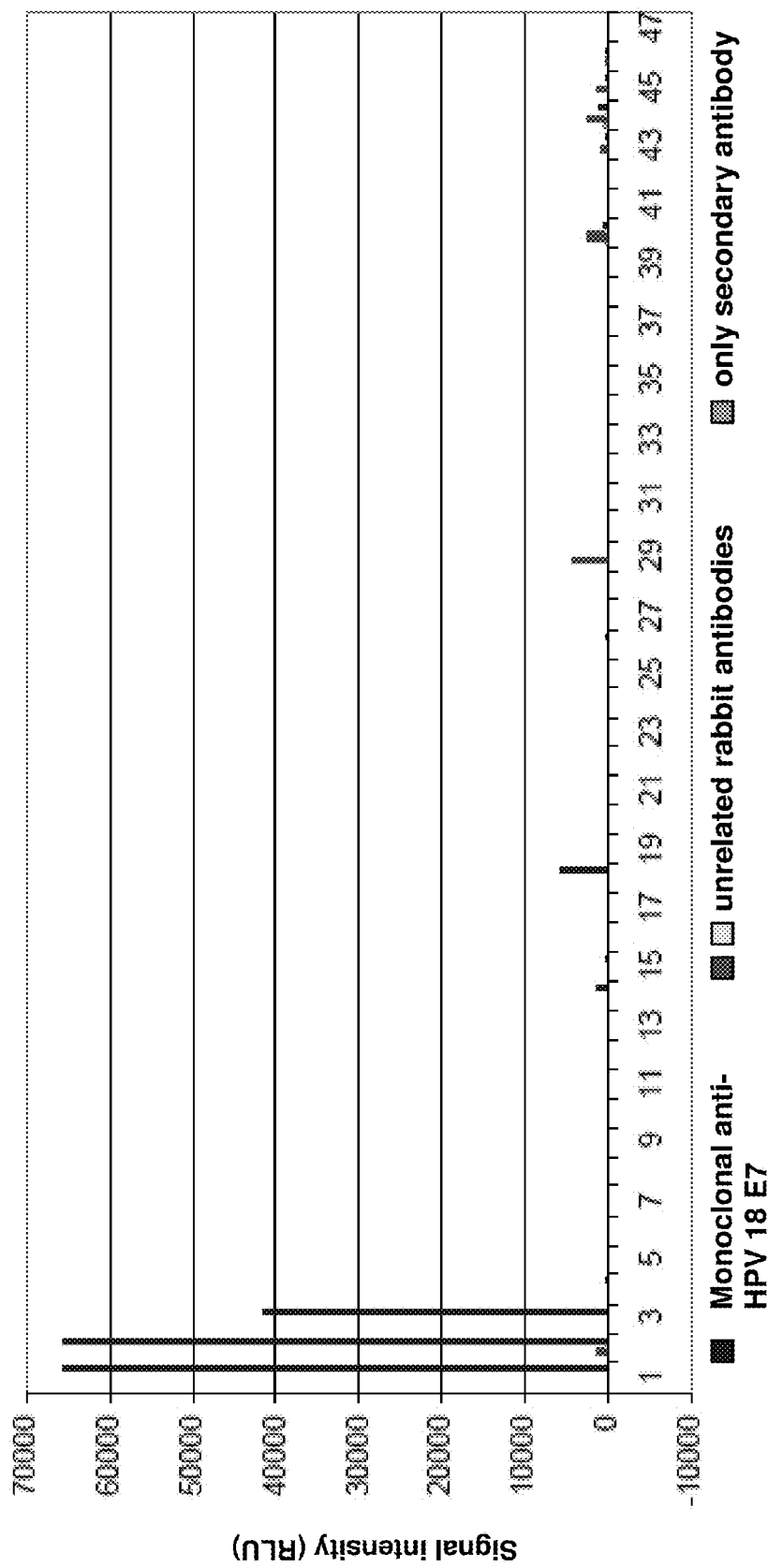

SEQUENCE LISTING

```
<160> NUMBER OF SEQ ID NOS: 10

<210> SEQ ID NO 1
<211> LENGTH: 5
<212> TYPE: PRT
<213> ORGANISM: HPV 16 and 18 subtypes E7
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Val Cys Pro Xaa Cys
1               5

<210> SEQ ID NO 2
<211> LENGTH: 10
<212> TYPE: PRT
<213> ORGANISM: HPV 16 subtypes E7
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 2

Gly Xaa Xaa Xaa Xaa Val Cys Pro Xaa Cys
1               5                   10

<210> SEQ ID NO 3
<211> LENGTH: 13
<212> TYPE: PRT
<213> ORGANISM: HPV16-E7

<400> SEQUENCE: 3

Gly Thr Leu Gly Ile Val Cys Pro Ile Cys Ser Gln Lys
1               5                   10

<210> SEQ ID NO 4
<211> LENGTH: 10
<212> TYPE: PRT
<213> ORGANISM: HPV 18 subtype E7
```

```
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 4

Phe Val Cys Pro Xaa Cys Ala Xaa Xaa Gln
1               5                   10

<210> SEQ ID NO 5
<211> LENGTH: 9
<212> TYPE: PRT
<213> ORGANISM: HPV18-E7

<400> SEQUENCE: 5

Lys Ala Thr Leu Gln Asp Ile Val Leu
1               5

<210> SEQ ID NO 6
<211> LENGTH: 12
<212> TYPE: PRT
<213> ORGANISM: HPV16-E7

<400> SEQUENCE: 6

Thr Leu Gly Ile Val Cys Pro Ile Cys Ser Gln Lys
1               5                   10

<210> SEQ ID NO 7
<211> LENGTH: 13
<212> TYPE: PRT
<213> ORGANISM: HPV16-E7

<400> SEQUENCE: 7

Thr Leu Gly Ile Val Cys Pro Ile Cys Ser Gln Lys Pro
1               5                   10

<210> SEQ ID NO 8
<211> LENGTH: 10
<212> TYPE: PRT
<213> ORGANISM: HPV 18 E7

<400> SEQUENCE: 8

Pro Lys Ala Thr Leu Gln Asp Ile Val Leu
1               5                   10

<210> SEQ ID NO 9
<211> LENGTH: 1380
<212> TYPE: DNA
<213> ORGANISM: Oryctolagus cuniculus

<400> SEQUENCE: 9
atggagactg ggctgcgctg gcttctcctg gtcgctgtgc tcaaaggtgt ccagtgtcag      60
tcgctggagg agtccggggg tcgcctggta acgcctggag ggtccctgac actcacctgc     120
acagtctctg gaatcgacct cagtacctat gaaataagct gggtccgcca ggctccaggg     180
aaggggctgg aatggatcgg aatcattggt actagcgcta acacagtcta cgcgagctgg     240
gcgaaaggcc gattcaccat ctccaaatcc tcgaccacgg tggatctgag ggtgaccagt     300
ctgacaaccg aggacacggc cacctatttc tgtgcccgtg cctacgatga atatggtatt     360
catgcttttc atccctgggg cccaggcacc ctggtcaccg tctcctcagg caacctaag      420
```

-continued

```
gctccatcag tcttcccact ggcccctgc tgcgggaca cacccagctc cacggtgacc    480
ctgggctgcc tggtcaaagg gtacctcccg gagccagtga ccgtgacctg gaactcgggc    540
accctcacca atggggtacg caccttcccg tccgtccggc agtcctcagg cctctactcg    600
ctgagcagcg tggtgagcgt gacctcaagc agccagcccg tcacctgcaa cgtggcccac    660
ccagccacca acaccaaagt ggacaagacc gttgcgccct cgacatgcag caagcccacg    720
tgcccacccc tgaactcct gggggaccc tctgtcttca tcttccccc aaaacccaag    780 gacaccctca tgatctcacg cacccccgag gtcacatgcg tggtggtgga cgtgagccag    840
gatgaccccg aggtgcagtt cacatggtac ataaacaacg agcaggtgcg caccgcccgg    900
ccgccgctac gggagcagca gttcaacagc acgatccgcg tggtcagcac cctccccatc    960 gcgccaccagg actggctgag gggcaaggag ttcaagtgca aagtccacaa caaggcactc    1020 ccggcccca tcgagaaaac catctccaaa gccagagggc agccctgga gccgaaggtc    1080 tacaccatgg gccctcccg ggaggagctg agcagcaggt cggtcagcct gacctgcatg    1140
atcaacggct tctaccttcc cgacatctcg gtggagtggg agaagaacgg gaaggcagag    1200
gacaactaca agaccacgcc ggccgtgctg gacagcgacg gctcctactt cctctacagc    1260
aagctctcag tgcccacgag tgagtggcag cggggcgacg tcttcacctg ctccgtgatg    1320
cacgaggcct tgcacaacca ctacacgcag aagtccatct cccgctctcc gggtaaatga    1380
```

<210> SEQ ID NO 10
<211> LENGTH: 720
<212> TYPE: DNA
<213> ORGANISM: Oryctolagus cuniculus

<400> SEQUENCE: 10

```
atggacacga gggccccccac tcagctgctg gggctcctgc tgctctggct cccaggtgcc     60
acatttgccc aagtgctgac ccagactcca tcccctgtgt ctgcagctgt gggaggcaca    120
gtcaccatca actgccaggc cagtcagagt gtttataatg ccaaaaattt agcctggtat    180
cagcagaaac cagggcagcc tcccaagctc ctgatttacc aggcttccac tctggcatct    240
ggggtcccat cgcggttcaa aggcagtgga tctgggacac agttcactct caccatcagc    300
ggcgtgcagt gtgacgatgc tgccacttac tactgtcaag gcgaatttag ttgtagtagt    360
gctgattgta atgttttcgg cggagggacc gaggtggtgg tcaaaggtga tccagttgca    420
cctactgtcc tcatcttccc accagctgct gatcaggtgg caactggaac agtcaccatc    480
gtgtgtgtgg cgaataaata ctttcccgat gtcaccgtca cctgggaggt ggatggcacc    540
acccaaacaa ctggcatcga aacagtaaa acaccgcaga attctgcaga ttgtacctac    600
aacctcagca gcactctgac actgaccagc acacagtaca acagccacaa agagtacacc    660
tgcaaggtga cccagggcac gacctcagtc gtccagagct tcaataggg tgactgttag    720
```

ANTI-HPV E7 ANTIBODIES

CROSS-REFERENCE TO RELATED APPLICATIONS

Figure 1:
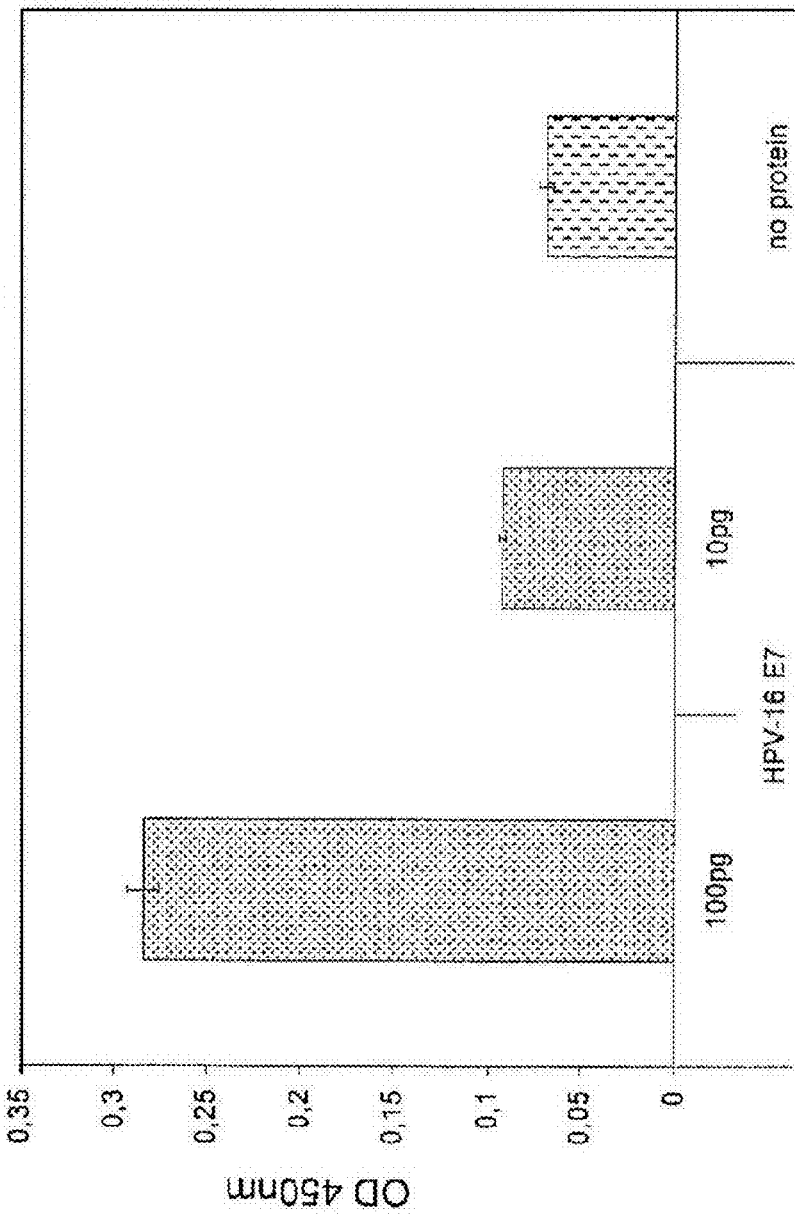
Figure 1:
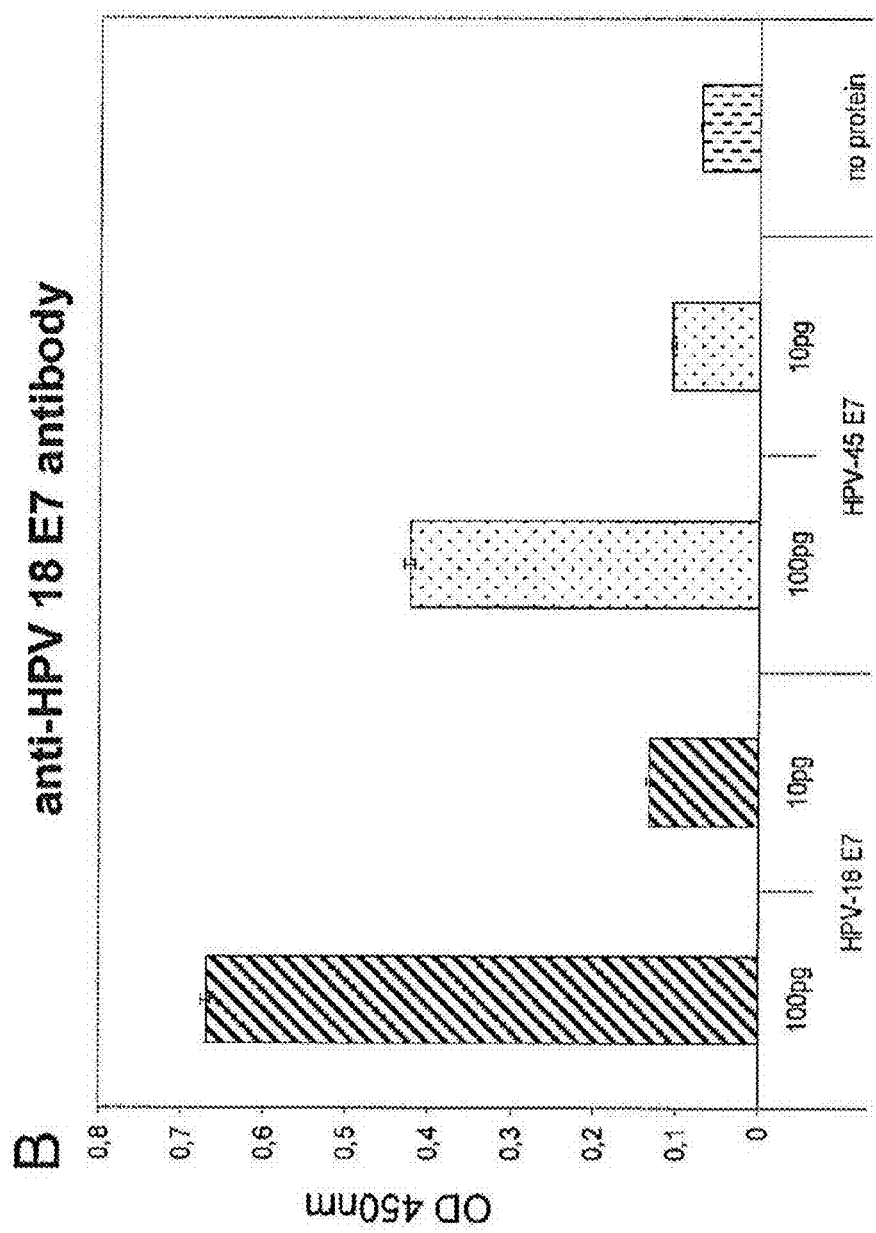

This application is a 371 U.S. National Stage of International Application No. PCT/EP2011/000728, filed Feb. 16, 2011. This application claims priority to European Patent Applications No. EP 10001569.2, filed Feb. 16, 2010 and EP 10011978.3, filed Sep. 30, 2010. The disclosures of the above applications are incorporated herein by reference.

The present invention relates to monoclonal anti-HPV (human papillomavirus) E7 antibodies capable of specifically recognising an epitope of the C-terminal or the N-terminal region of a HPV E7 protein, diagnostic compositions and kits comprising said antibodies as well as methods for immunohistochemical and ELISA-based diagnosis of HPV infections utilizing said antibodies.

Sexually transmitted infections with human papillomaviruses (HPVs) are the main etiological factor for cervical cancer. Over forty, in particular over thirty-five HPV genotypes, that can infect epithelial squamous and glandular cells in the cervical mucosa, have been described. On the basis of epidemiological and biochemical data, the double stranded DNA HPVs are divided into high-risk HPVs associated with squamous intraepithelial lesions with a high potential for progression to invasive squamous cell carcinoma, and low-risk HPVs associated with benign hyperplasia. Infections by high-risk genotypes have been detected in almost all neoplastic lesions of the cervix and at least 15 high-risk types of HPV have been associated with cervical cancer. HPV 16 is the most prevalent genotype worldwide with an incidence in squamous cell carcinoma of approximately 55%, followed by HPV 18 (approximately 17%) and HPV 45 (4-9%).

The persistence of oncogenic HPV is necessary for the development of cervical precancer and cancer. However, the factors that determine viral persistence and tumorigenic progression are not fully understood. The initial events of cervical carcinogenesis after viral infection depend on the fact that high-risk HPV types undergo specific changes that abrogate the transcriptional control of viral gene expression in the infected keratinocytes. Inactivation of these cellular control functions permits deregulated transcription of the early viral genes E6 and E7, thereby triggering cell proliferation, inhibition of apoptosis, reprogramming of differentiation and chromosomal instability. These changes can support the integration of episomal HPV genomes into chromosomes of the host cell, and contribute to further overexpression of the viral genes E6 and E7, resulting in an increase of the E7 oncoprotein levels during early steps of cervical carcinogenesis.

That the viral oncoproteins E6 and E7 are crucial during carcinogenesis was further proven by the fact that high-risk E7 protein, in cooperation with high-risk E6, can efficiently immortalize human primary keratinocytes in vitro. Moreover, the consistent overexpression of the E6 and E7 oncogenes is required to induce and to maintain the transformed phenotype of cervical cancer cells.

Thus, overexpression of E7 oncoproteins of carcinogenic HPV types is a characteristic feature of cervical cancer. This conclusion is supported by a recent study where affinity-purified antibodies against high-risk HPV E7 proteins were used to detect the E7 oncoproteins of HPV 16, 18 and 45 in biopsies from invasive cervical squamous cell carcinoma patients (Ressler et al., 2007, Clin Cancer Res, 13:7067-7072), indicating that the high-risk E7 oncoproteins of these major high-risk HPV types are expressed continuously in invasive cervical carcinoma.

At present, clinical cervical cancer screening is mainly based on the cytological assessment of cells contained in cervical smears, referred to as Pap Smears (or Papanicolaou test; Papanicolaou, 1942, Science, 95:438-439), that are routinely taken from women participating in screening programs. The result of the cytological analysis is dependent on detection of abnormal cells by experienced pathologists. Although the implementation of this simple and efficient assay has helped to considerably reduce the mortality of cervical cancer, Pap Smear diagnosis is still characterized by a high rate of false-positive and false-negative results (Foucar, 2005, Semin Diagn Pathol, 22(2):147-155).

In an alternative approach, detection of high-risk HPV DNA has been introduced into clinical practice. In this setting, a sensitive DNA detection assay (e.g., Hybrid Capture 2™; Digene Inc., USA) is applied to determine the presence of high-risk HPV DNA in patient samples. Although this assay is well suited to detect infections by papillomaviruses of the high-risk type, it cannot discriminate between transient infections, which spontaneously regress in most cases, and the onset of cervical cancer. More recently, diagnostic systems have been developed that detect the presence of E6/E7 mRNA in cervical smears, as a surrogate marker for the expression of the viral oncoproteins E6 and E7. However, it has been shown that the level of E6/E7 mRNA is not significantly changing during carcinoma progression, suggesting that RNA detection may not be the best tool for cervical cancer screening (Hafner et al., 2008, Oncogene, 27(11): 1610-1617). In accordance with this notion, the underlying HPV infection could not be detected by PCR analysis in all examined tumors by Ressler et al., 2007.

Therefore, the detection of E7 protein seems to be the superior diagnostic tool. Various antibodies are already known in the art, but they either display low sensitivity or specificity or are described to cross-react with the E7 proteins of various HPV types. Also, as polyclonal antibodies can only be produced in a limited quantity by one animal, there are batch-to-batch differences. The difficulty to produce highly specific and sensitive monoclonal antibodies against E7 proteins is mainly due to the low immunogenicity of E7 proteins.

WO 07/059,492 for example, discloses methods, assays and kits for the detection of HPV DNA or proteins, employing inter alia monoclonal and polyclonal antibodies against the HPV 16 E7 protein, capable of reliably detecting the rather high amount of around 1 μg of recombinant HPV 16 E7 protein.

Accordingly, the technical problem underlying the present invention is to overcome the aforementioned difficulties and to provide highly specific and more sensitive means for a cost-efficient, rapid and reliable diagnosis of high-risk HPV infections.

The present invention solves its underlying problem according to the teaching of the independent claims. Accordingly, the present invention provides monoclonal antibodies against the E7 proteins of high-risk HPV types, in particular provides a monoclonal anti-HPV (human papillomavirus) E7 antibody, which is capable of specifically recognising an epitope, in particular a conformation-specific epitope, of the C-terminal region of a HPV E7 protein.

The term "antibody" as employed herein preferably refers to a full immunoglobulin, like an IgG, IgA, IgM, IgD or IgE but in another embodiment may also refer to a fragment of an antibody, like an F(ab), F(abc), Fv, Fc or F(ab)$_2$ or a fused antibody, a fused antibody fragment or another derivative of the antibody of the present invention as long as it still displays the specificity and sensitivity of the full immunoglobulin of the present invention.

The term "specificity" or "specifically recognising/binding" is understood to refer to the property of an antibody to specifically recognise or bind to preferably only one specific epitope and preferably shows no or substantially no cross-reactivity to another epitope. Preferably "specificity" or "specifically recognising/binding" means that the antibody specifically recognises or binds to preferably only one specific epitope and preferably shows no or substantially no cross-reactivity to another epitope, wherein said epitope is unique for one protein, such that the antibody shows no or substantially no cross-reactivity to another epitope and another protein.

The term "sensitivity" as employed herein refers to the detection limit of an antibody, which is preferably low, i.e. at least below a concentration of 1 µg of the protein to be detected.

In general, the term "epitope" refers to an antigenic region of a given protein which consists of 4 to 50, preferably 5 to 15, preferably 8 to 11 amino acids, or more. This antigenic region or epitope is specifically recognised by the antigen binding site(s) of the antibody.

In the context of the present invention, the term "C-terminal region" is understood to refer to the at most 30, 35, 40, 45, 50, 55 or 60 C-terminal amino acids of the HPV E7 protein.

In a preferred embodiment, the monoclonal anti-HPV E7 antibody specifically recognises an epitope of the zinc finger domain of the C-terminal region of the HPV E7 protein, preferably said epitope is a conformational epitope.

The monoclonal antibodies according to the present invention are preferably used to detect native, i.e. non-denatured HPV E7 proteins.

In the context of the present invention, the term "conformational epitope" refers to a three-dimensional epitope which the antibody specifically recognises or binds to as opposed to a linear epitope. Linear epitopes are determined solely by the amino acid sequence, whereas conformational epitopes are determined by the three-dimensional surface features, i.e. the tertiary structure. Therefore, the amino acids of a conformational epitope defining the antigenicity of a protein do not necessarily have to be consecutive amino acids of the protein but can be distant from each other in the primary protein sequence to form the conformational epitope, only if the protein is folded in its tertiary structure. Mostly, such conformational epitopes cannot be recognised by the antibody, if the protein is denatured, i.e. not folded into its tertiary structure.

HPV E7 proteins contain a zinc finger domain in their C-terminal part, which forms a highly ordered rigid structure, mainly due to 4 cystein residues. These cystein residues coordinate zinc and thereby represent a conformational epitope. Surprisingly, it has been found that the monoclonal antibodies according to the present invention which are capable of recognising or binding to such a conformational epitope, are able to detect a HPV E7 protein in a highly specific and highly sensitive manner.

In a preferred embodiment, the monoclonal antibody is capable of specifically recognising an epitope of the C-terminal region, preferably the zinc finger domain, of the E7 protein of HPV 16 subtypes, in particular HPV types 16, 31, 33, 35, 52, 58 or of HPV 18 subtypes, in particular HPV types 18, 39, 45, 59, 68, 70 or of both HPV 16 and 18 subtypes. Preferably, the recognised epitope is a conformational epitope. Preferably, the recognised epitope comprises the amino acid sequence set forth in SEQ ID No. 1 which is a common epitope sequence motif present in epitopes of the present invention. The epitope motif characterised by SEQ ID No. 1 represents a consensus epitope motif for HPV 16 and 18 subtypes and is: Val Cys Pro Xaa Cys, with Xaa being any amino acid.

The term "consensus epitope motif" as employed herein refers to specific parts of an epitope which are shared by the E7 proteins of HPV 16 and/or 18 subtypes. Despite sharing such a consensus epitope motif, the C-terminal regions of HPV 16 and/or 18 subtypes, in particular the specific epitopes contained therein and containing this epitope motif are, due to specific amino acid sequences and/or a specific conformation of the amino acid sequence, substantially different enough, so that specific antibodies are able to specifically recognise a particular E7 protein from a specific HPV type, i.e. are capable of identifying specifically one particular HPV type.

In a preferred embodiment of the present invention, the monoclonal antibody is capable of specifically recognising an epitope of the C-terminal region, preferably the zinc finger domain, of HPV 16 subtypes, in particular 16, 31, 33, 35, 52 and 58. Preferably, the recognised epitope is a conformational epitope. Preferably, the recognised epitope comprises the amino acid sequence set forth in SEQ ID No. 2 which is a common sequence motif present in epitopes of the HPV 16 subtypes. The epitope motif characterised by the amino acid sequence of SEQ ID No. 2 represents a consensus epitope motif specific for HPV 16 subtypes, and is: Gly Xaa Xaa Xaa Xaa Val Cys Pro Xaa Cys, with Xaa being any amino acid.

In a particularly preferred embodiment of the present invention, the monoclonal antibody is capable of specifically recognising the E7 protein of HPV 16. Preferably, the recognised epitope comprises, preferably consists of, the amino acid sequence set forth in SEQ ID No. 3. The epitope characterised by the amino acid sequence of SEQ ID No. 3 represents a specific conformational epitope of the zinc finger domain in the C-terminal part of the HPV 16 E7 protein, and is: Gly Thr Leu Gly Ile Val Cys Pro Ile Cys Ser Gln Lys. These amino acids represent positions 85 to 97 of the HPV 16 E7 protein. A further particularly preferred embodiment of the conformational epitope is represented by the amino acid sequence of SEQ ID No. 7 and is: Thr Leu Gly Ile Val Cys Pro Ile Cys Ser Gln Lys Pro. These amino acids represent positions 86 to 98 of the HPV 16 E7 protein. The amino acid sequence of SEQ ID No. 6 represents a specifically preferred embodiment of the conformational epitope of SEQ ID No. 3 and 7 and is: Thr Leu Gly Ile Val Cys Pro Ile Cys Ser Gln Lys. These amino acids represent positions 86 to 97 of the HPV 16 E7 protein. All of these epitope sequences comprise two of the four cystein residues which coordinate the zinc ion of the zing finger domain in two CXXC motifs. Epitope mapping using microarrays with HPV 16 E7 derived synthetic 13 mer peptides identified this epitope to be recognised by the monoclonal antibody of the present invention very specifically (see FIG. 10). An alignment of HPV E7 protein sequences suggested that especially the amino acids upstream and downstream of the highly conserved 90VCPXC94 motif within the epitope of SEQ ID No. 3, 6 and 7 provide the specific recognition of the HPV 16 E7 protein by the monoclonal antibody of the present invention.

A mutational analysis showed that peptides containing a point mutation in the zinc coordination site could not be detected by the monoclonal antibody against the E7 protein of HPV 16, whereas deletion mutants of other regions could be readily detected. This clearly indicates that an intact zinc finger domain, representing a conformational epitope, is necessary for the specific recognition of HPV 16 E7 protein by the monoclonal antibody according to the present invention. This is best illustrated by the inability of the monoclonal antibody against HPV 16 E7 of the present invention to recognise the HPV 16 E7 mutant C58G, wherein the cystein residue at position 58 is changed to glycine, containing the sequence required to recognise the linear epitope but has lost the ability to provide this epitope in a conformational zinc finger domain.

In accordance with the conformational nature of the epitope of SEQ ID No. 3 and 7, in particular SEQ ID No. 6, the monoclonal antibody recognising this epitope has to be used in much higher concentrations (e.g. 15 µg/ml to detect 10 ng of purified protein) in applications like Western blot or protein recognition in cell lysates, where the proteins are denatured, than known polyclonal antibodies against HPV 16 E7.

This epitope, preferably C-terminal conformational epitope, lies within a region of the E7 protein usually displaying low immunogenicity. Surprisingly, it could be shown that the monoclonal antibody recognising the epitope as given in SEQ ID No. 3 and 7, in particular SEQ ID No. 6, is able to specifically detect the E7 protein of HPV 16 in a highly sensitive manner and does not cross-react with E7 proteins of other HPV types, preferably in non-denaturing applications. In particular, the monoclonal antibody against HPV 16 E7 did not cross react with the E7 proteins of HPV 18 or HPV 45, when these proteins were overexpressed in U-2OS cells. Also, the monoclonal antibody against HPV 16 E7 strongly detected endogenous E7 protein of HPV 16 positive CaSki cells in immunofluorescence experiments. In contrast, no signal was observed in untransfected U-2OS cells or in HPV 18 positive HeLa cells. To more precisely characterise the cross reaction of the monoclonal antibody against HPV 16 E7 an ELISA assay using E7 proteins of different HPV types was employed. Also, no cross reactivity was found against the E7 proteins of other HPV types such as other high risk HPV genotypes and the two most common low risk HPV types, HPV 6 and HPV 11.

Further, preincubation of the monoclonal antibody against HPV 16 E7 with the purified HPV 16 E7 protein prevented the detection of cell associated HPV 16 E7, since the antibody was already specifically bound to the preincubated HPV 16 E7 protein.

Compared to the prior art, the present monoclonal antibody is at least 20 times, in particular at least 100 times, more sensitive with no loss of specificity. As infections with HPV 16 account for over 50% of cervix carcinoma cases worldwide, the highly specific antibody according to the present invention is suitable to serve as a highly effective and reliable diagnostic tool. Advantageously, it could be shown that the monoclonal anti-HPV 16 E7 antibody according to the present invention is able to detect low amounts such as 1 pg, in particular 500 fg, of HPV 16 E7 protein in an ELISA-based assay (enzyme-linked immunosorbant assay), whereas the antibodies disclosed in WO 07/059,492 could only detect concentrations of HPV 16 E7 protein of about 1 µg. The monoclonal anti-HPV 16 E7 antibody according to the present invention can therefore be used in much lower concentrations, for example 10 pg/µl, which renders its application as a diagnostic tool also more cost-effective.

Using the present monoclonal antibody against HPV 16 E7 it could also be shown that subcellular localisation of HPV 16 E7 protein varies during cell cycle between predominantly cytoplasmic and predominantly nuclear.

It has been shown that E7 protein levels increase from undetectable to substantial levels during carcinogenesis. With the highly sensitive monoclonal antibodies according to the invention it is possible to detect not only tumor cells of squamous cell carcinoma and adenocarcinomas, but also cells of high-grade precancerous cervical intraepithelial neoplasia and carcinoma in situ (CIN III and CIS) as well as cervical intraepithelial glandular neoplasia grade III and adenocarcinoma in situ (CIGN III and AIS), which were reported to have a high potential to progress to invasive cancer. This might advantageously permit early diagnosis of high-grade precancerous CIN III, CIS, CIGN III, ACIS, and AIS before their progression to malignant tumors, as the monoclonal antibodies according to the present invention can discriminate between low grade precancerous lesions of squamous cell and glandular origin (CIN I-II, CIGN I-II) on the one hand, and high-grade precancers (CIN III, CIS, CIGN III) and cancers (CxCa, AdCa) of squamous cell and glandular origin on the other hand. Thus, the monoclonal antibodies according to the present invention can serve as a new tool to identify high-grade precancers and cancers of squamous cell and glandular origin.

Thus, the present invention preferably relates to a monoclonal antibody specifically recognising an epitope comprising the amino acid sequence of SEQ ID No. 1, 2, 3 and 4, preferably comprising or consisting of SEQ ID No. 3 and 7, in particular SEQ ID No. 6.

Preferably, the monoclonal antibody according to the present invention which is capable to specifically recognise the E7 protein of HPV 16, preferably capable of recognising an epitope with the amino acid sequence of SEQ ID No. 3 and 7, in particular SEQ ID No. 6, comprises, preferably consists of a heavy chain having the cDNA sequence of SEQ ID No. 9 or a light chain having the cDNA sequence of SEQ ID No. 10 or both.

Thus, the present invention relates to a monoclonal antibody or fragment thereof, wherein said antibody or antibody fragment comprises an amino acid sequence coded by at least one of SEQ ID No. 9 or 10. This encompasses also mutated versions of SEQ ID No. 9 or 10, i.e. sequences that comprise additions, deletions and/or substitutions of single or multiple nucleotides compared to SEQ ID No. 9 or 10 as long as the antibody or antibody fragment coded by the mutated sequence still displays the specificity and sensitivity of the full immunoglobulin of the present invention.

The present invention also relates to a hybridoma cell line, preferably a mammalian, most preferred a rabbit hybridoma cell line, capable of producing the above-identified monoclonal antibody according to the invention, in particular of the antibody capable to specifically recognising the E7 protein of HPV 16, preferably capable of recognising an epitope of the C-terminal region of HPV 16, in particular a conformational epitope, preferably an epitope with the amino acid sequence of SEQ ID No. 3 and 7, in particular SEQ ID No. 6. The present invention preferably relates to the hybridoma cell line deposited as Kion 42-3-78 at the Leibniz Institute DSMZ-German Collection of Microorganisms and Cell Cultures on Dec. 16, 2009. which has the accession no. DSM ACC3034. In a preferred embodiment the present invention also relates to the monoclonal antibody, which is obtainable from the supernatant of a hybridoma cell line according to the present invention.

The term "hybridoma cell line" as employed herein refers to a cell line obtained by fusing myeloma cells, preferably immortalized, mammalian, in particular rabbit, lymphoid cells with B-cells of the spleen of a mammal, preferably a rabbit that has been immunized with the desired antigen, i.e. a purified HPV E7 protein. Such an immortal hybridoma cell line is able to produce one specific and defined type of antibody which is secreted into the cell culture medium or supernatant. The term "monoclonal" refers to the cell line from which the antibody is obtained, wherein all the cells are clones of a single parent cell. This permits advantageously standardized production and purification procedures to obtain monoclonal antibodies of the same quality.

Furthermore, such hybridoma cell lines can be grown indefinitely in the suitable cell culture media thereby providing an infinite source of the monoclonal antibody, without batch-to-batch variations. This is particularly advantageous for an application of monoclonal antibodies in clinical diagnostic routines, as time-consuming tests of new antibody batches can be omitted and diagnostic methods produce constant and reliable results.

In a preferred embodiment of the present invention, the monoclonal antibody is capable of specifically recognising an epitope of the C-terminal region, preferably the zinc finger domain, of HPV 18 subtypes, in particular 18, 39, 45, 59, 68 and 70. Preferably, the recognised epitope is a conformational epitope. Preferably, the epitope comprises the amino acid sequence set forth in SEQ ID No. 4, which is a common sequence motif present in epitopes of the HPV 18 subtypes and is: Phe Val Cys Pro Xaa Cys Ala Xaa Xaa Gln, with Xaa being any amino acid.

The epitope motif characterised by the amino acid sequence of SEQ ID No. 4 represents a consensus epitope motif of the HPV 18 subtypes.

In another aspect, the present invention relates to a monoclonal anti-HPV E7 antibody, which is capable of specifically recognising an epitope of the N-terminal region of a human papillomavirus E7 protein. In a preferred embodiment, the monoclonal antibody of this aspect of the present invention is capable of specifically recognising an epitope of the N-terminal region of the E7 protein of HPV 16 subtypes, in particular HPV types 16, 31, 33, 35, 52, 58 or of HPV 18 subtypes, in particular HPV types 18, 39, 45, 59, 68, 70 or of both HPV 16 and 18 subtypes.

The term "N-terminal region" as employed herein refers to the at most 30, 35, 40, 45, 50, 55 or 60 N-terminal amino acids of the HPV E7 protein.

In a particularly preferred embodiment the monoclonal antibody specifically recognises an epitope of the N-terminal region of the E7 protein of HPV 18 subtypes, in particular HPV types 18, 39, 45, 59, 68, 70, preferably of HPV 18, HPV 45 or both. Preferably, the antibody specifically recognising the N-terminal region of HPV 18 E7 protein shows cross-reactivity with HPV 11, 45, 56, 58, 59 and 70. In particular, the antibody specifically recognising the N-terminal region of HPV 18 E7 protein shows a high level of cross-reactivity with HPV 18, 45 and 56, an intermediate level of cross-reactivity with HPV 6 and 39, and a low level of cross-reactivity with HPV 11, 33, 52, 58, and 59 with the respective E7 proteins transiently overexpressed by U-2OS cells in an immunofluorescence assay. In an ELISA-based assay, however, it could be shown that the monoclonal antibody according to the present invention capable of specifically recognising an epitope of the N-terminal region of the HPV 18 E7 protein only substantially crossreacts with the E7 protein of HPV 45. Also, the monoclonal antibody according to the present invention capable of specifically recognising an epitope of the N-terminal region was able to strongly detect endogenous E7 protein of HPV 18 positive HeLa cells, whereas no signal was obtained in untransfected U-2OS cells or in HPV 16 positive CaSki cells, in both immunofluorescence and western blot experiments.

Preferably, the recognised specific N-terminal epitope comprises, preferably consists of, the amino acid sequence set forth in SEQ ID No. 5 and is: Lys Ala Thr Leu Gln Asp Ile Val Leu. These amino acids represent positions 5 to 13 of the HPV 18 E7 protein. A further particularly preferred embodiment of the N-terminal epitope is represented by the amino acid sequence of SEQ ID No. 8 and is: Pro Lys Ala Thr Leu Gln Asp Ile Val Leu. These amino acids represent positions 4 to 13 of the HPV 18 E7 protein.

Advantageously, it could be shown that the monoclonal anti-HPV 18 E7 antibody according to the present invention is able to detect low amounts such as 1 pg, in particular 500 fg, of HPV 18 E7 protein in an ELISA-based assay.

The present invention also relates to a hybridoma cell line, preferably a mammalian, most preferred a rabbit, hybridoma cell line, capable of producing the monoclonal antibody capable of specifically recognising an epitope of the N-terminal region of the HPV 18 E7 protein, preferably capable of recognising an epitope with the amino acid sequence of SEQ ID No. 5 or 8. The present invention preferably relates to the hybridoma cell line deposited as Klon 143-7-33 at the Leibniz Institute DSMZ-German Collection of Microorganisms and Cell Cultures on Dec. 16, 2009, which has the accession no. DSM ACC3035. In a preferred embodiment the present invention also relates to the monoclonal antibody, which is obtainable from the supernatant of a hybridoma cell line according to the present invention.

In a particularly preferred embodiment, the monoclonal antibodies according to the present invention are mammalian, preferably rabbit, monoclonal antibodies (RabMabs), preferably produced by a rabbit hybridoma cell line. Due to a more sophisticated immune system, rabbits are able to produce more elaborate antibodies than mice. This advantage combined with the possibility to create rabbit hybridoma cell lines makes it possible to obtain high quality monoclonal antibodies.

For various applications the monoclonal antibodies according to the present invention may be detectably labelled themselves with a radioactive, enzymatic or fluorescent group. A variety of techniques is available for labelling biomolecules such as antibodies, which are well-known to the person skilled in the art. Commonly used labels comprise inter alia fluorochromes, like fluorescein, rhodamine, Texas Red, Cy3 or Cy5, enzymes like peroxidase, horse radish peroxidase, β-galactosidase, alkaline phosphatase or acetylcholinesterase, radioactive isotopes, digoxygenin, colloidal metals, chemi- or bioluminescent compounds. Preferably, the monoclonal antibodies according to the present invention are labelled with biotin. In another preferred embodiment, the antibodies of the present invention are detected by secondary methods, like indirect immunofluorescence. Accordingly, detectably labelled secondary antibodies may be employed to specifically detect the monoclonal antibodies according to the present invention.

In a preferred embodiment, the present invention also relates to a diagnostic composition, comprising the monoclonal antibodies according to the present invention as an active agent. Said diagnostic composition may, in a preferred embodiment, comprise the monoclonal antibody of the present invention in soluble form or liquid phase. In another preferred embodiment the present antibodies are bound, attached and/or linked to a solid support. In another preferred embodiment, the present diagnostic composition comprises the monoclonal antibodies according to the invention formulated with a diagnostically acceptable carrier, diluent, buffer or storage solution. The diagnostic composition of the present invention comprises in a preferred embodiment the monoclonal antibodies individually or in combinations according to the requirements of the intended application. Preferably, said diagnostic composition is used for the immunological, preferably immunohistological, immunofluorescence- or ELISA-based detection of HPV E7 protein in a biological sample to enable the diagnosis of HPV infections.

The present invention also relates to a diagnostic kit, comprising the monoclonal antibodies according to the invention as a first agent and other antibodies directed against HPV E7 proteins as a second agent. The antibodies used as a second agent are preferably polyclonal goat antibodies, capable of recognising the E7 proteins of high-risk HPV 16, 18, 31, 33, 35, 39, 45, 52, 56, 58 and 59.

The diagnostic kit of the present invention comprises in a preferred embodiment the monoclonal antibodies individually or in combinations according to the requirements of the intended application.

The diagnostic kit according to the present invention is preferably used for immunological, preferably immunohistochemical, immunofluorescence- or ELISA-based detection of HPV E7 protein, thereby enabling the diagnosis of HPV infections. Preferably, the diagnostic kit of the present invention further comprises optionally one or more buffers, storage solutions and/or other reagents or materials required for medical, scientific or diagnostic purposes. Furthermore, parts of the diagnostic kit can be packaged individually in vials or bottles or in combination in containers or multi-container units.

The use of the monoclonal antibodies according to the present invention in an in vitro method, in particular an immunological, preferably immunohistochemical or immunofluorescence-based in vitro method or an ELISA-based, preferably direct or sandwich ELISA, in vitro method is also contemplated by the present invention. Also, the monoclonal antibodies according to the present invention might be advantageously used in a test strip, for example a lateral flow test, for the detection of HPV E7 proteins.

Thus, in a preferred embodiment the present invention relates to an in vitro method for the detection of HPV E7 protein, comprising i) incubating a biological sample with the monoclonal antibody according to the present invention and ii) measuring and/or detecting HPV E7 protein in the biological sample by measuring and/or detecting the antibody specifically bound to the E7 protein.

In a particularly preferred embodiment, the present invention provides an in vitro method for the immunological, preferably immunohistochemical or immunofluorescence-based diagnosis of HPV infections, comprising a) incubating a biological sample with the monoclonal antibodies according to the present invention and b) measuring and/or detecting HPV E7 protein, preferably the E7 protein of high-risk HPV types, in the biological sample by measuring and/or detecting the antibody specifically bound to the E7 protein and thereby allowing the diagnosis of a HPV infection. Advantageously, the application of the monoclonal antibodies according to the present invention in such a diagnostic method allows for a highly sensitive and reliable detection of high-risk HPV infections, as the monoclonal antibodies according to the present invention display a very high signal-to-noise ratio with negligible background. In a preferred embodiment, the monoclonal anti-HPV E7 antibody capable of specifically recognising an epitope of the C-terminal or N-terminal region of the HPV E7 protein is used in this method. Preferably, the monoclonal antibody against the C-terminus of HPV 16 E7 according to the present invention is used in this method, since it shows no cross-reactivity with other HPV types and a very high sensitivity.

The term "biological sample" as employed herein is understood to refer to any kind of biological tissue, cells and/or organs, preferably cervix biopsies or smears, preferably Pap Smears.

In yet another particularly preferred embodiment, the present invention relates to an in vitro method for the ELISA-based diagnosis of HPV infections, comprising aa) coating a support with capture antibodies directed against HPV E7 proteins, bb) adding a biological sample, preferably a cell lysate, to the coated support, cc) incubating the support with the monoclonal detection antibody according to the present invention, and dd) identifying HPV E7 protein specifically bound by the capture antibodies by measuring and/or detecting the monoclonal detection antibody specifically bound to the E7 protein and thereby allowing the diagnosis of a HPV infection, preferably high-risk HPV infection. In a preferred embodiment, the monoclonal anti-HPV E7 antibody capable of specifically recognising the C-terminal or N-terminal region of the HPV E7 protein is used as detection antibody in this method. Preferably, the monoclonal antibody against the N-terminus of HPV 18 E7 according to the present invention is used, preferably as detection or capture antibody in this method. When used as detection antibody in this method, the antibodies according to the present invention are preferably biotinylated, since this leads to an increase in specificity and sensitivity of the HPV E7 detection.

Preferably, polyclonal goat antibodies are used as capture antibodies for the ELISA-based diagnosis method, which are capable of recognising the E7 proteins of high-risk HPV types 16, 18, 31, 33, 35, 39, 45, 52, 56, 58 and 59. As these polyclonal goat antibodies only bind E7 proteins of high-risk HPV types, the application of the anti-HPV 16 E7 antibody and the anti-HPV 18 E7 antibody as detection antibodies advantageously allows the detection of high-risk HPV types 16, 18, 45, 56, 58, 59 and 70 which together account for >95% of all cervical cancers.

As support or solid support ELISA-plates are preferably used but different carriers or materials may as well be chosen by the person skilled in the art.

Cell lysates to be tested with the ELISA-based method are preferably prepared from biological samples, preferably cervix biopsies or smears, preferably Pap Smears.

Further preferred embodiments are the subject matter of the subclaims.

The sequence listing shows:

SEQ ID No. 1 shows the amino acid sequence of a C-terminal consensus epitope motif of the E7 protein of HPV 16 subtypes and HPV 18 subtypes and SEQ ID No. 2 shows the amino acid sequence of a C-terminal consensus epitope motif of the E7 protein of HPV 16 subtypes and SEQ ID No. 3 shows the amino acid sequence of the C-terminal conformational epitope of the HPV 16 E7 protein, in particular comprising positions 85 to 97 of the HPV 16 E7 protein and SEQ ID No. 4 shows the amino acid sequence of a C-terminal consensus epitope motif of the E7 protein of HPV 18 subtypes and SEQ ID No. 5 shows the amino acid sequence of the N-terminal epitope of the HPV 18 E7 protein, in particular comprising positions 5 to 13 of the HPV 18 E7 protein and SEQ ID No. 6 shows the amino acid sequence of the C-terminal conformational epitope of the HPV 16 E7 protein comprising positions 86 to 97 of the HPV 16 E7 protein and SEQ ID No. 7 shows the amino acid sequence of the C-terminal conformational epitope of the HPV 16 E7 protein comprising positions 86 to 98 of the HPV 16 E7 protein and SEQ ID No. 8 shows the amino acid sequence of the N-terminal epitope of the HPV 18 E7 protein comprising positions 4 to 13 of the HPV 18 E7 protein and SEQ ID No. 9 shows the cDNA sequence of the heavy chain of the anti-HPV 16 E7 antibody of the present invention and SEQ ID No. 10 shows the cDNA sequence of the light chain of the anti-HPV 16 E7 antibody of the present invention.

The present invention is further illustrated by the following non-limiting examples and the accompanying figures.

The figures show:

FIG. 1 shows the sensitivity of the monoclonal antibodies of the present invention for the detection of recombinant E7 proteins by ELISA. ELISA plates were coated with a mixture (1:1) of goat polyclonal antibodies against HPV 16 E7 and HPV 18 E7. Then, recombinant E7 proteins were added in different concentrations. Subsequently, the monoclonal anti-HPV 16 E7 (1A) and anti-HPV 18 E7 (1B) antibodies of the present invention were added for the detection of the recombinant proteins bound by the goat polyclonal antibodies, followed by incubation with a corresponding secondary antibody for visualization.

Figure 2:
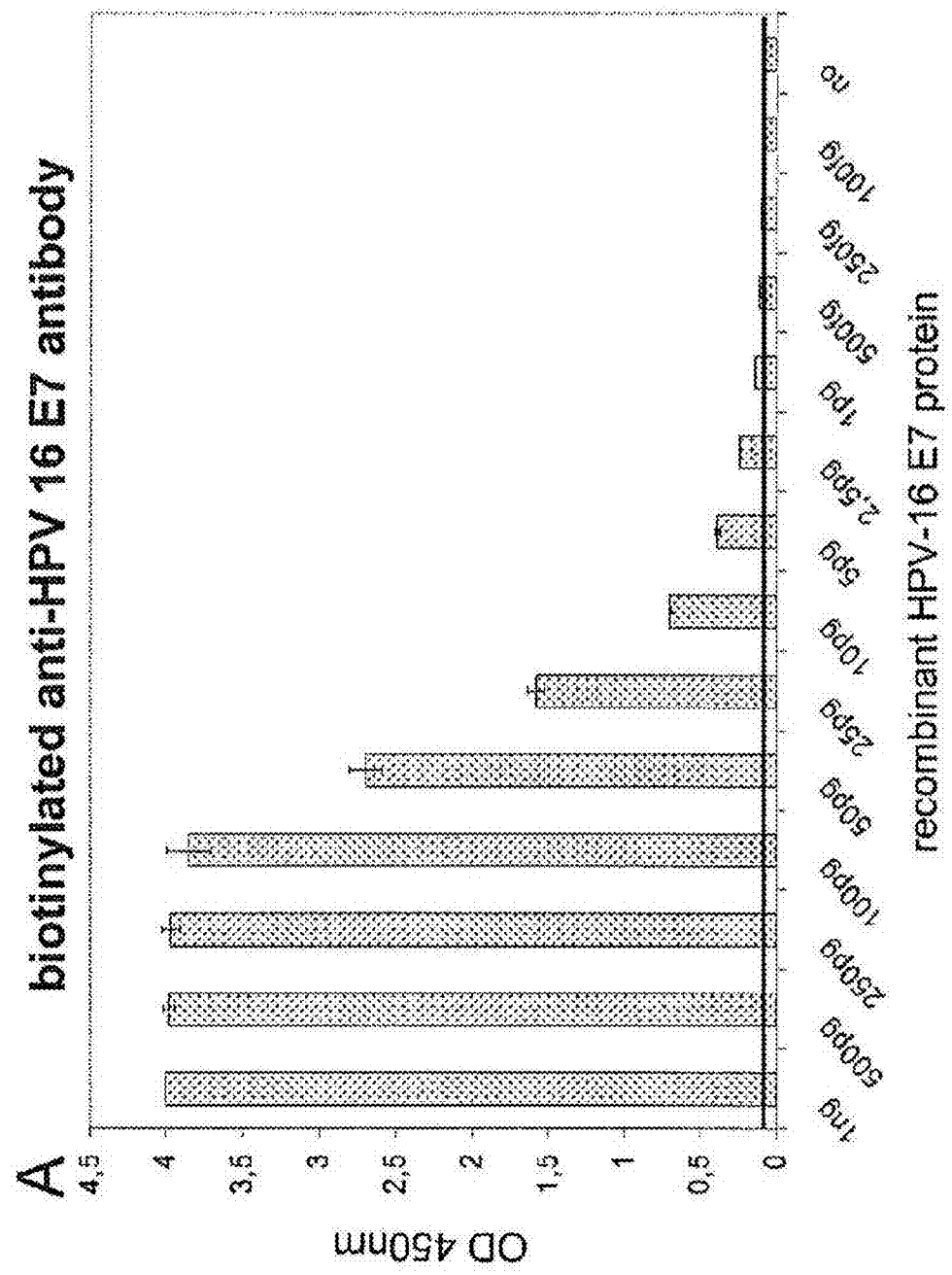
Figure 2:
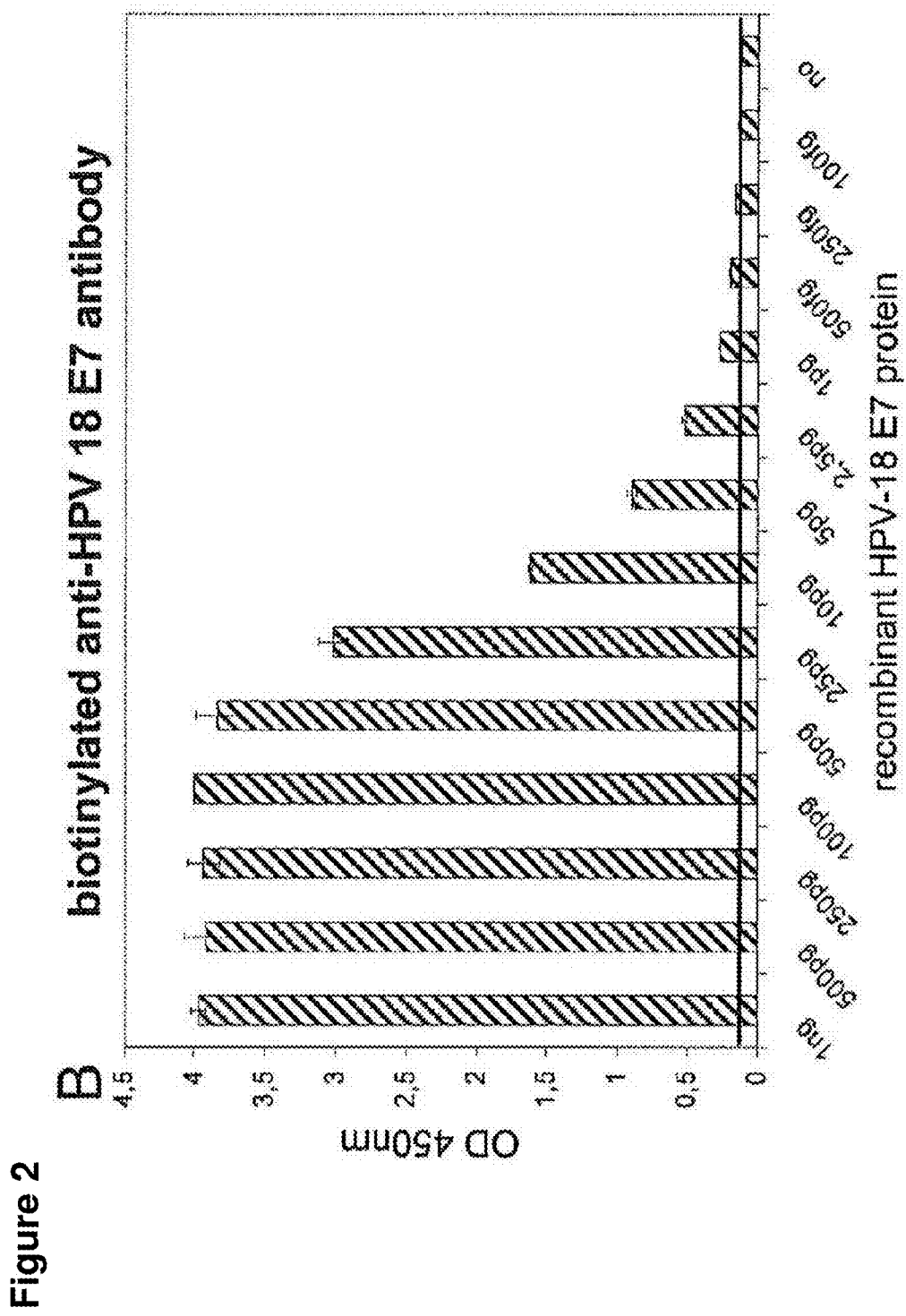
Figure 2:
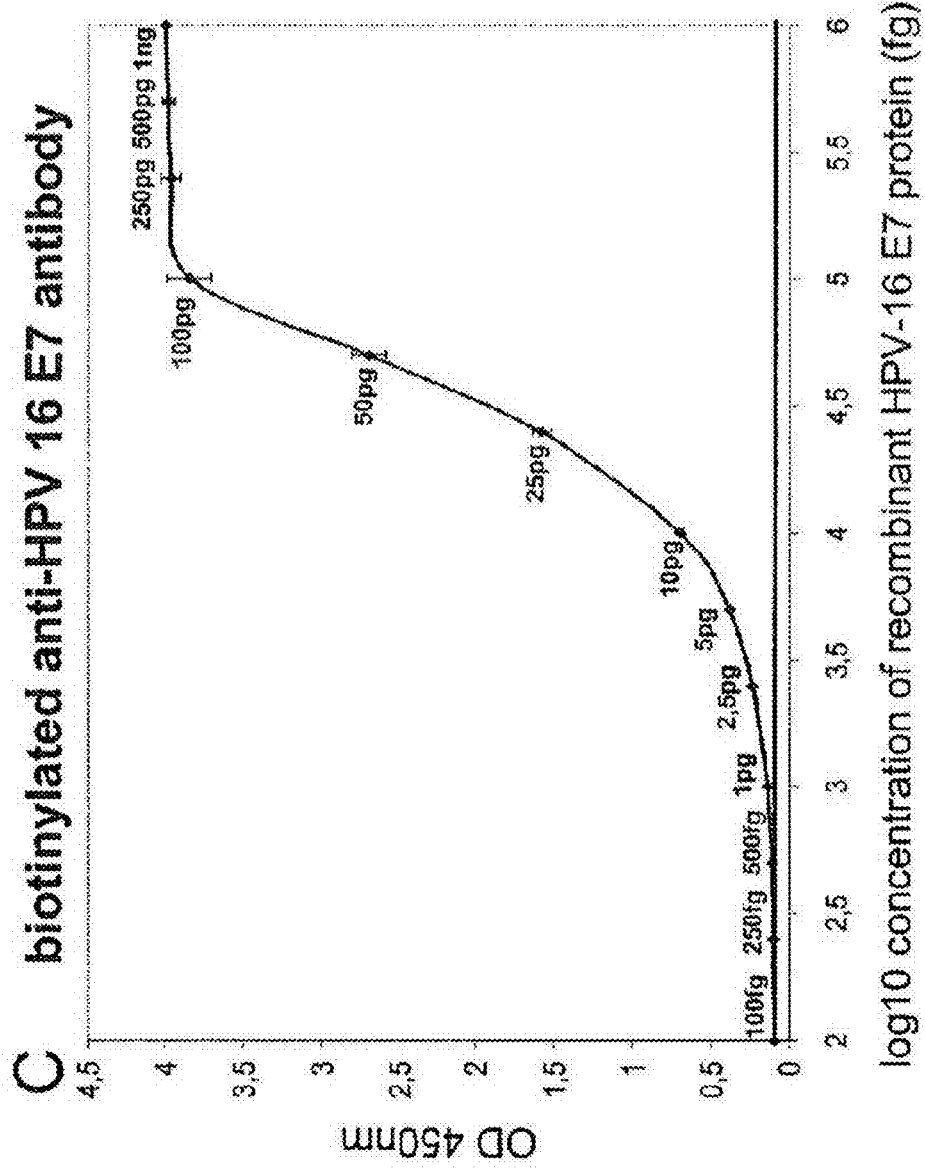
Figure 2:
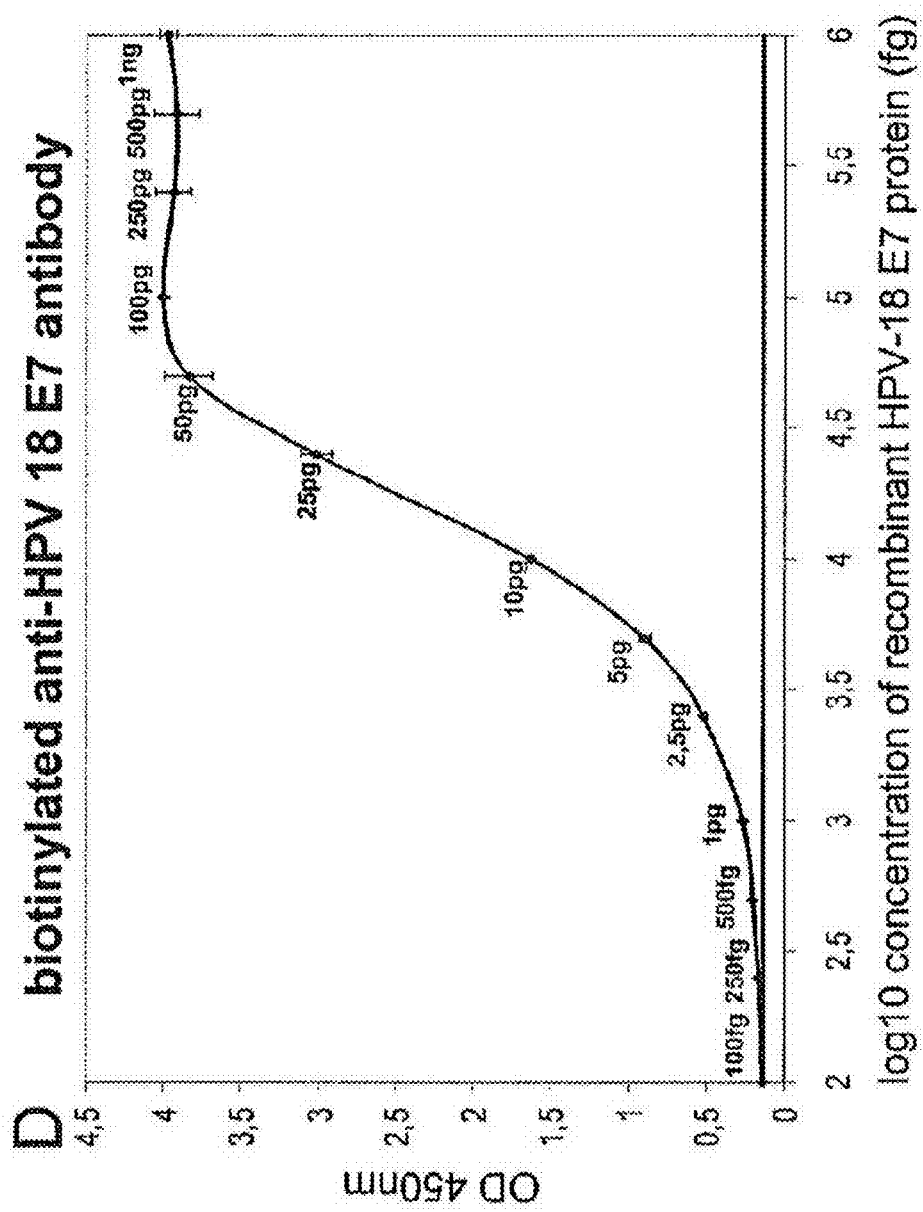

FIG. 2 shows the sensitivity of the biotinylated monoclonal antibodies of the present invention for the detection of recombinant E7 proteins by ELISA (2 A, B) and the logarithmic representation of the protein concentrations detected by the antibodies of the present invention (C, D). ELISA plates were coated with a mixture (1:1) of goat polyclonal antibodies against HPV 16 E7 and HPV 18 E7. Then, recombinant E7 proteins were added in different concentrations. Subsequently, the biotinylated monoclonal anti-HPV 16 E7 (2A, C) and anti-HPV 18 E7 (2B, D) antibodies of the present invention were added for detection of the E7 proteins bound by the goat polyclonal antibodies, followed by incubation with Streptavidin-Poly-HRP-conjugate for visualization. The detection limit is defined as mean of the background signal (twelve measurements) plus three times the standard deviation.

Figure 3:
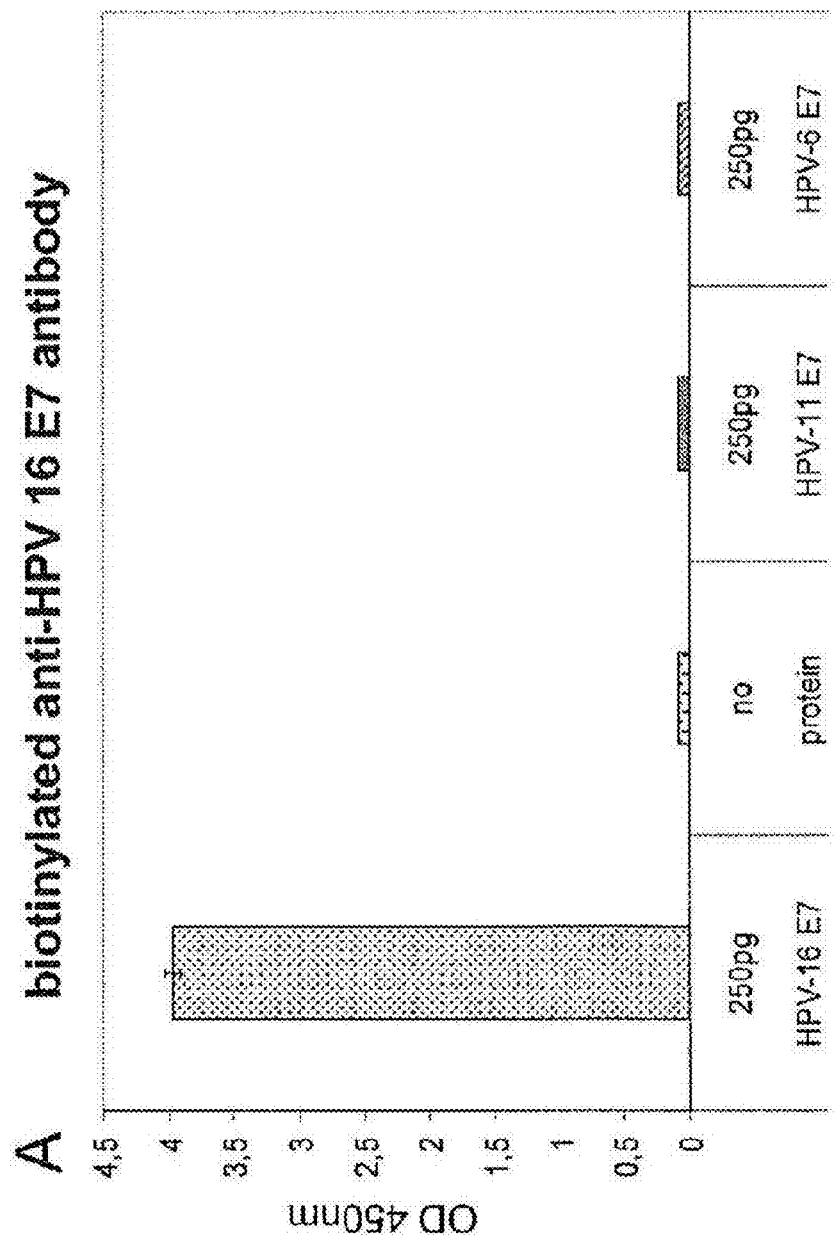
Figure 3:
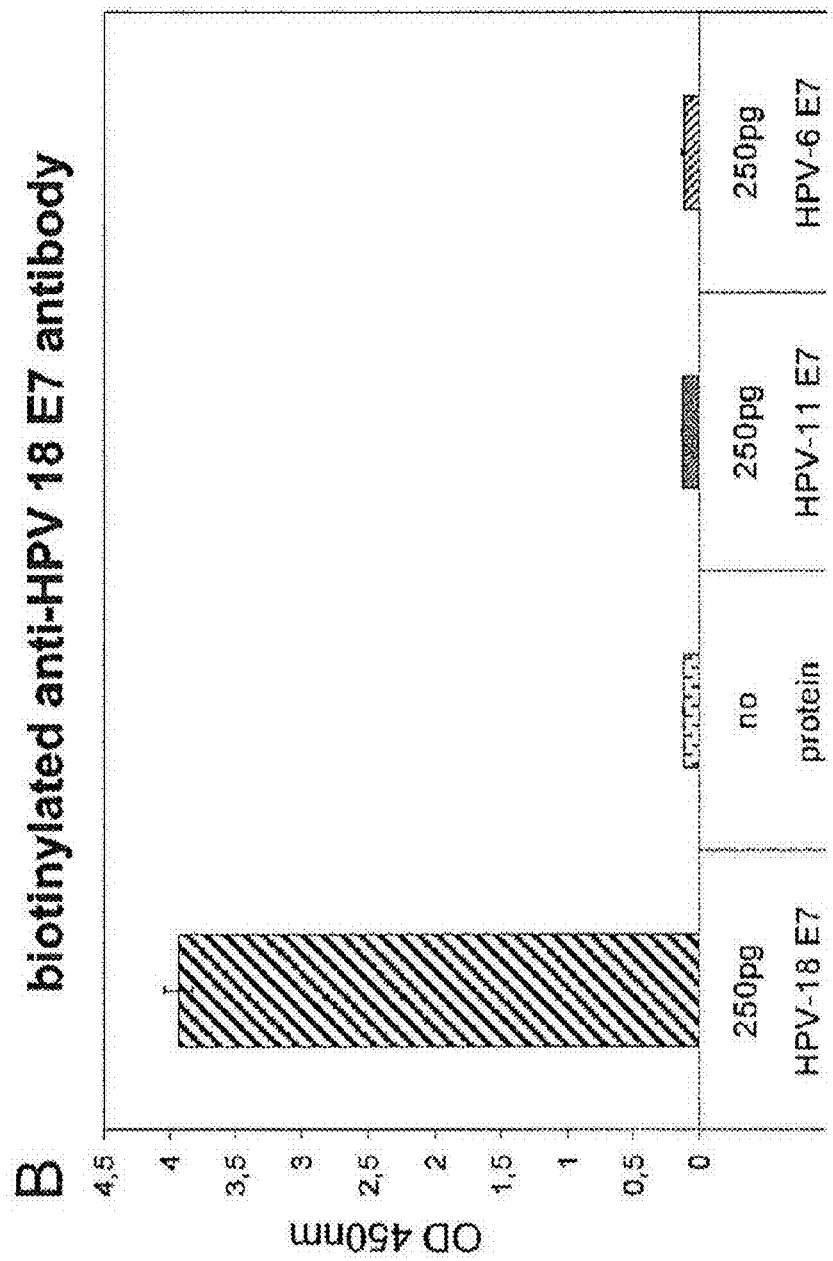

FIG. 3 shows that the biotinylated monoclonal antibodies of the present invention do not detect recombinant proteins of low-risk HPV types (6, 11) in an ELISA. ELISA plates were coated with a mixture (1:1) of goat polyclonal antibodies directed against HPV 16 E7 and HPV 18 E7. Then, different recombinant E7 proteins of high-risk HPV types (16, 18) and low-risk HPV types (6, 11) were added. Subsequently, the biotinylated monoclonal anti-HPV 16 E7 (3A) and anti-HPV 18 E7 (3B) antibodies of the present invention were added for the detection of the E7 proteins bound by the goat polyclonal antibodies, followed by incubation with Streptavidin-Poly-HRP-conjugate for visualization.

Figure 4:
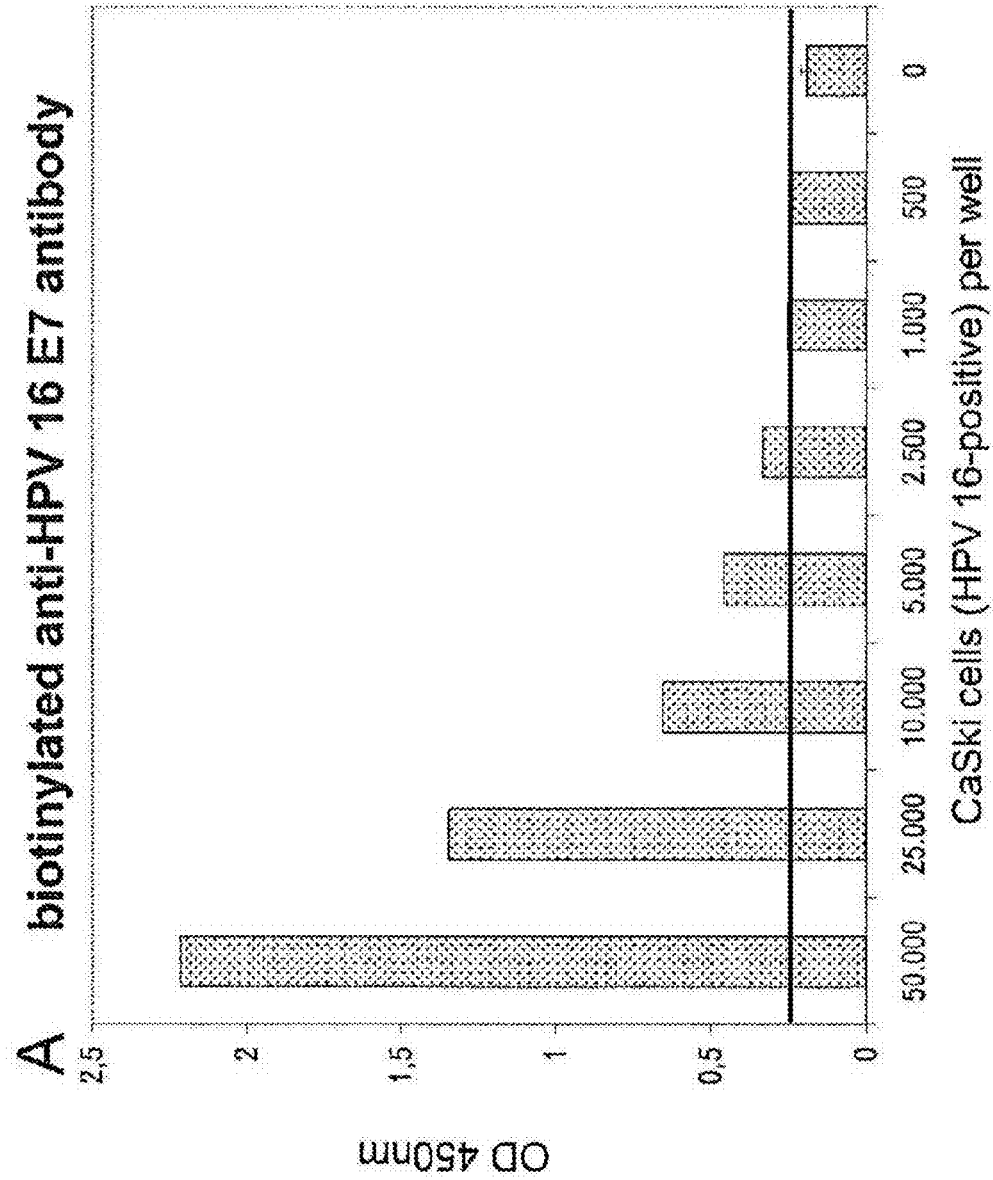
Figure 4:
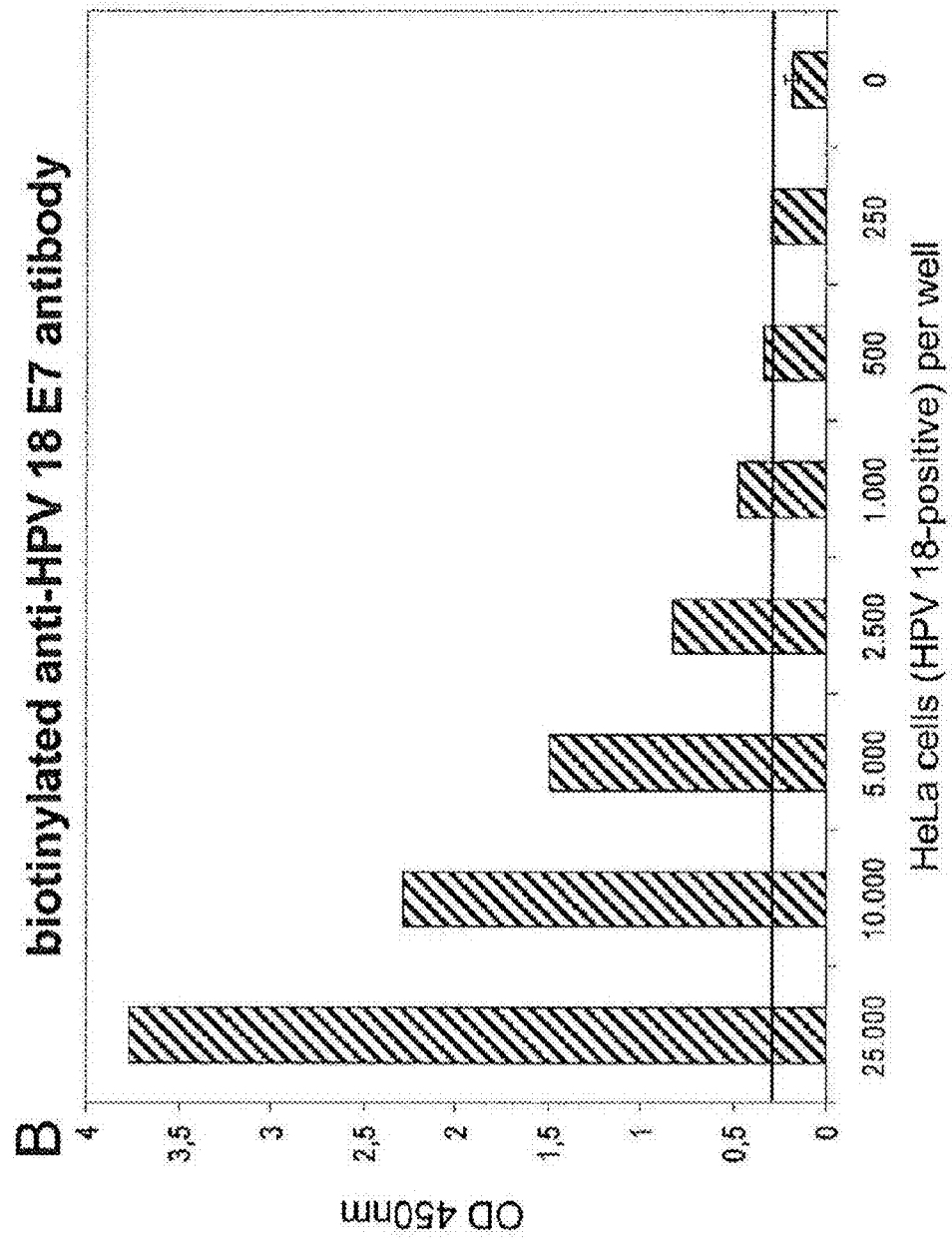

FIG. 4 shows the detection of endogenous E7 protein of CaSki-cells (HPV 16 positive) (4A) and HeLa-cells (HPV 18 positive) (4B) in the background of HPV negative U-2OS-cells with the biotinylated monoclonal antibodies of the present invention by ELISA. Therefore, ELISA plates were coated with a mixture (1:1) of goat polyclonal antibodies against HPV 16 E7 and HPV 18 E7. Cell lysates with a total cell concentration of 100,000 cells per well consisting of HPV negative U-2OS-cells as background and different amounts of HPV 16 E7 positive CaSki-cells or HPV 18 E7 positive HeLa-cells were added. Subsequently, the biotinylated monoclonal anti-HPV 16 E7 (4A) and anti-HPV 18 E7 (4B) antibodies of the present invention were added for the detection of E7 proteins bound by the goat polyclonal antibodies, followed by incubation with Streptavidin-Poly-HRP-conjugate for visualization. Detection limit is defined as mean of the background signal (12 measurements) plus three times the standard deviation.

Figure 5:
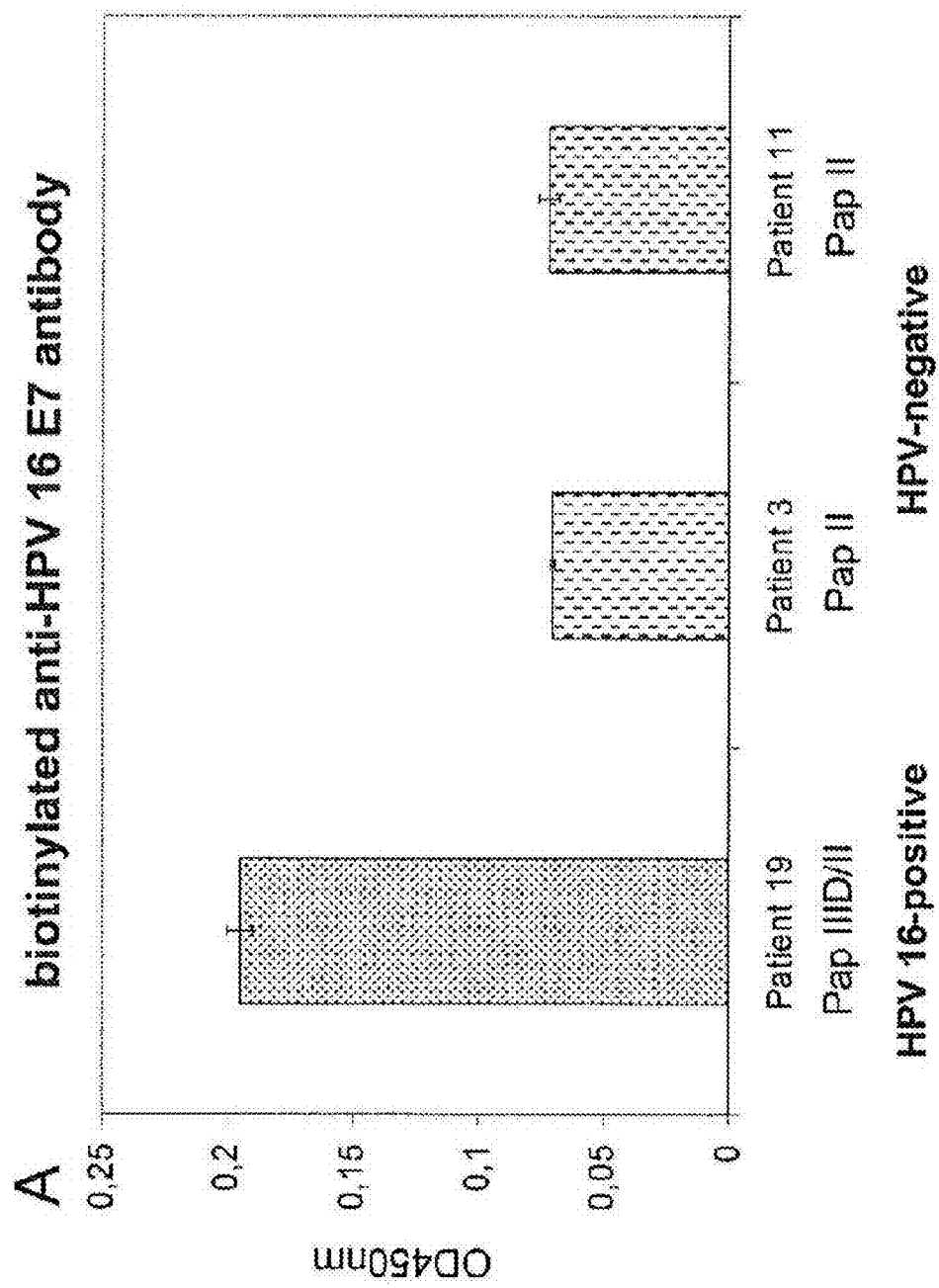
Figure 5:
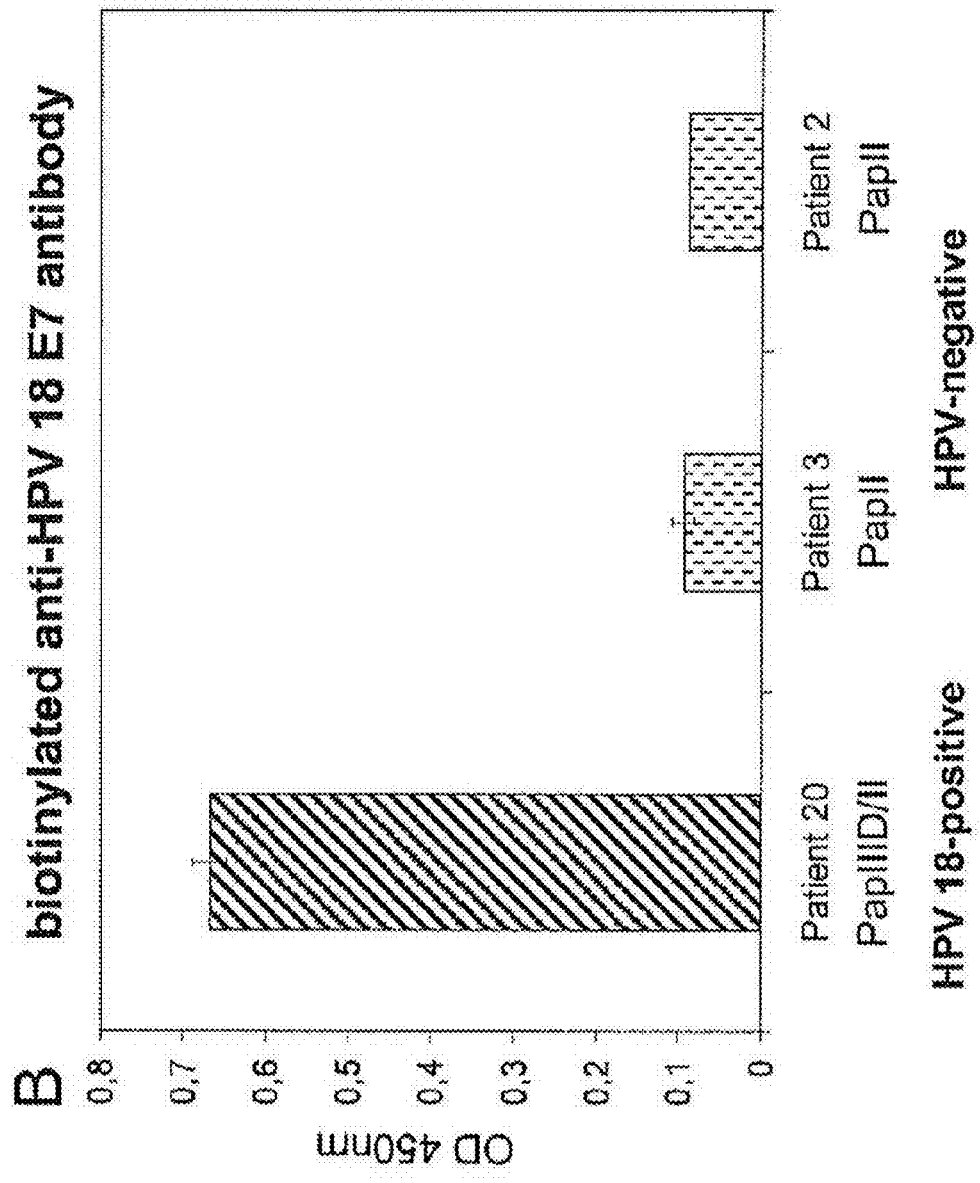

FIG. 5 shows the detection of E7 protein in five clinical samples (one HPV 16 positive, one HPV 18 positive and three HPV negative) with the biotinylated monoclonal antibodies of the present invention by ELISA. ELISA plates were coated with a mixture (1:1) of goat polyclonal antibodies against HPV 16 E7 and HPV 18 E7. Lysates of the clinical samples (100 μg/well) were added. Subsequently, the biotinylated monoclonal anti-HPV 16 E7 (5A) and anti-HPV 18 E7 (5B) antibodies of the present invention were added for the detection of E7 proteins bound by the goat polyclonal antibodies, followed by incubation with Streptavidin-Poly-HRP conjugate for visualization.

Figure 6:
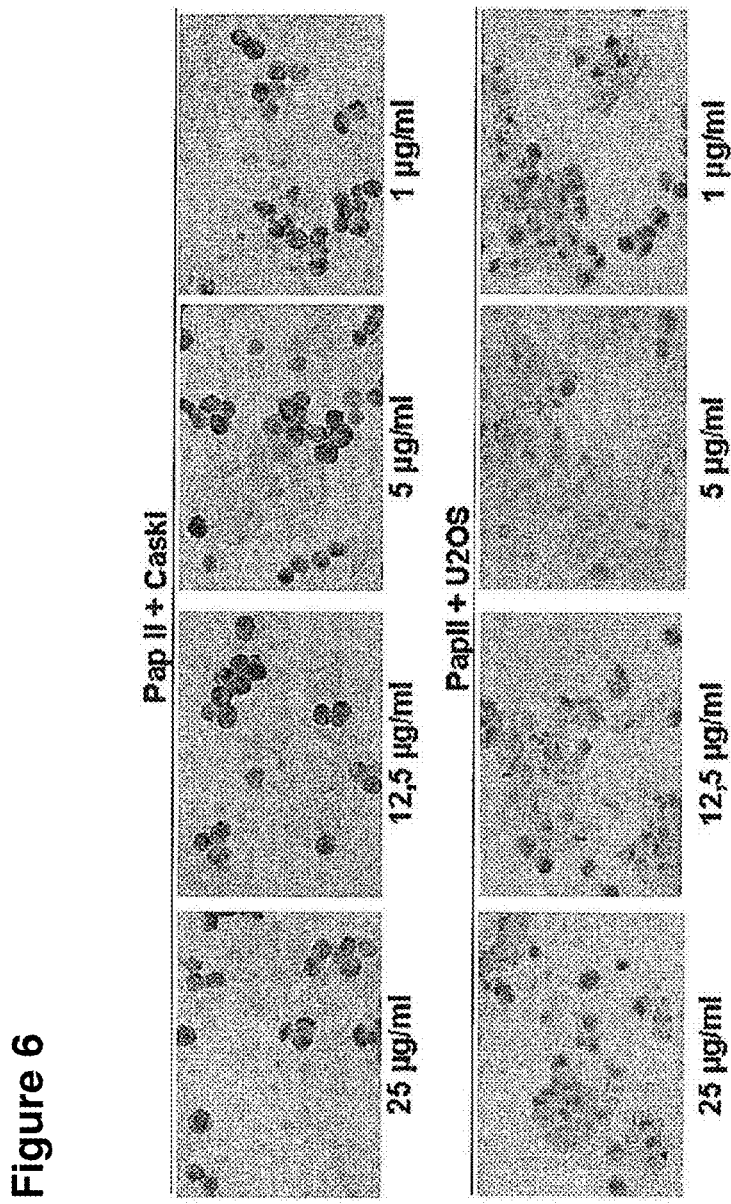

FIG. 6 shows the detection of E7 protein in LBC samples form healthy women spiked with CaSki cells (HPV 16 positive) and U-2OS cells (HPV negative). Liquid-based cytology was prepared from a cervical smear of a PapII proband, which did not yield any signal with anti-HPV 16 E7 antibody of the present invention. As indicated, 10,000 cells each of CaSki and U-2OS were added to the sample. HPV 16 E7 positive cells were specifically detected by immunohistochemistry with anti-HPV 16 E7 antibody of the present invention over a wide range of antibody dilutions, as indicated.

Figure 7:
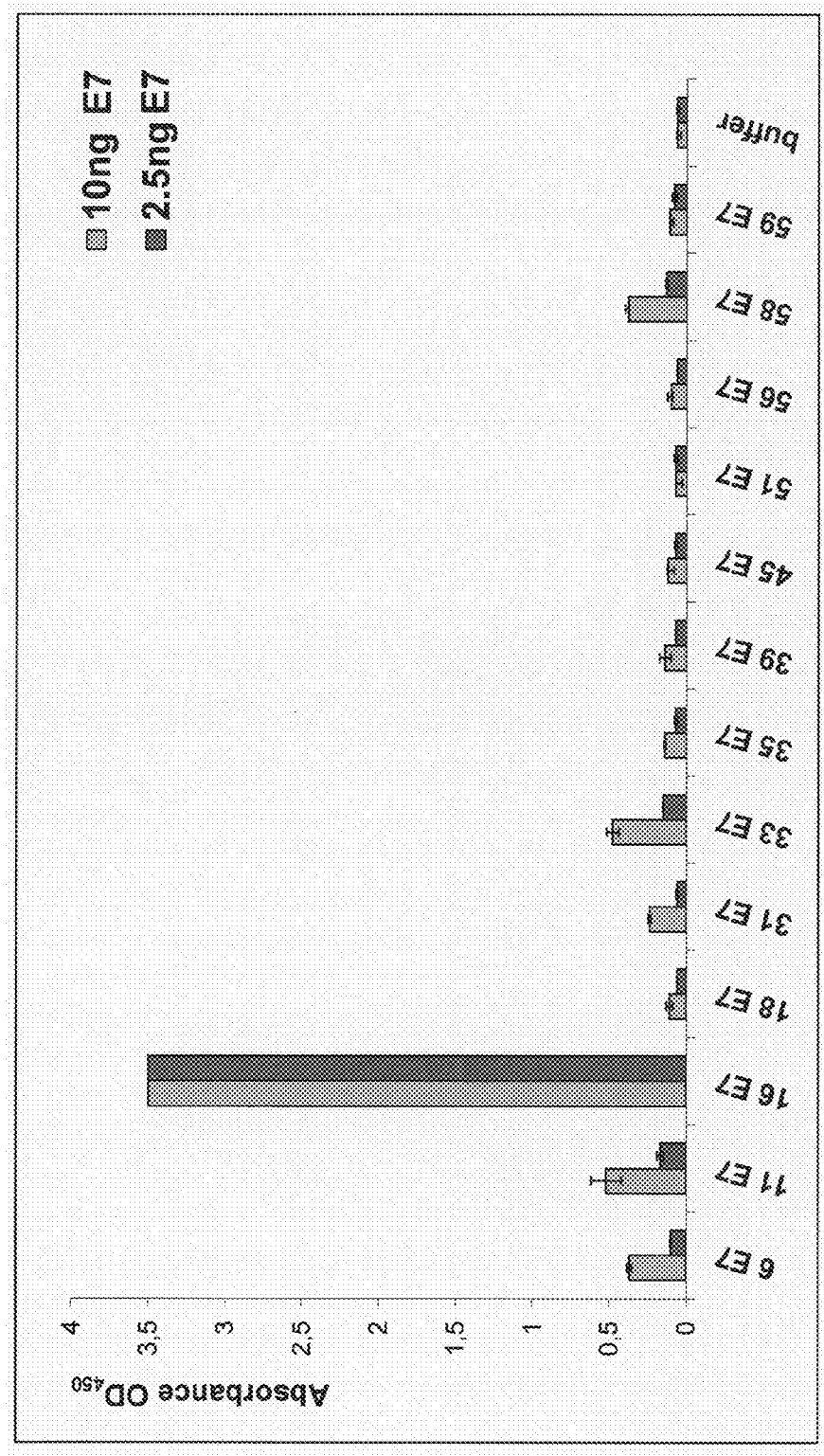

FIG. 7 shows the specificity of the monoclonal antibody against HPV 16 E7 employing a direct ELISA using 2.5 and 10 ng of randomly coated HPV E7 proteins of different HPV types detected by the biotinylated monoclonal antibody against HPV 16 E7 (14 ng/100 μl) with the buffer as a control.

Figure 8:
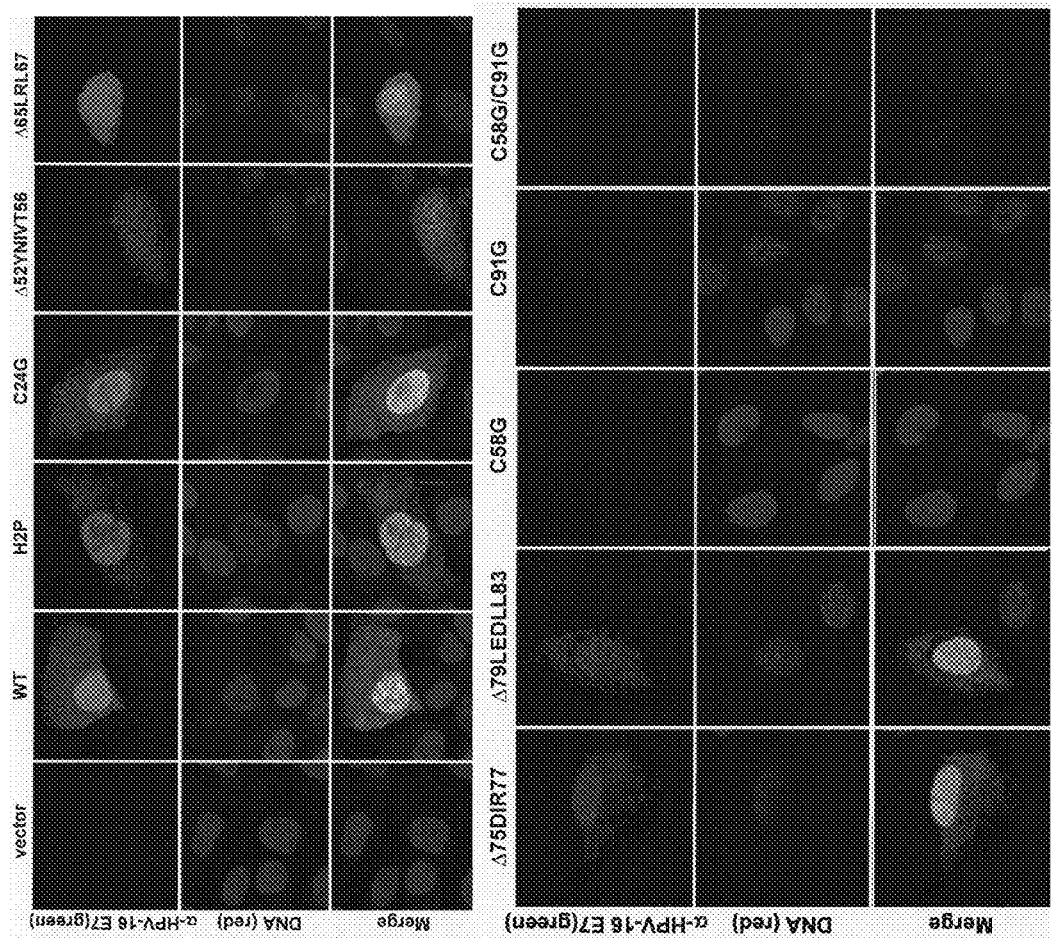
Figure 8:
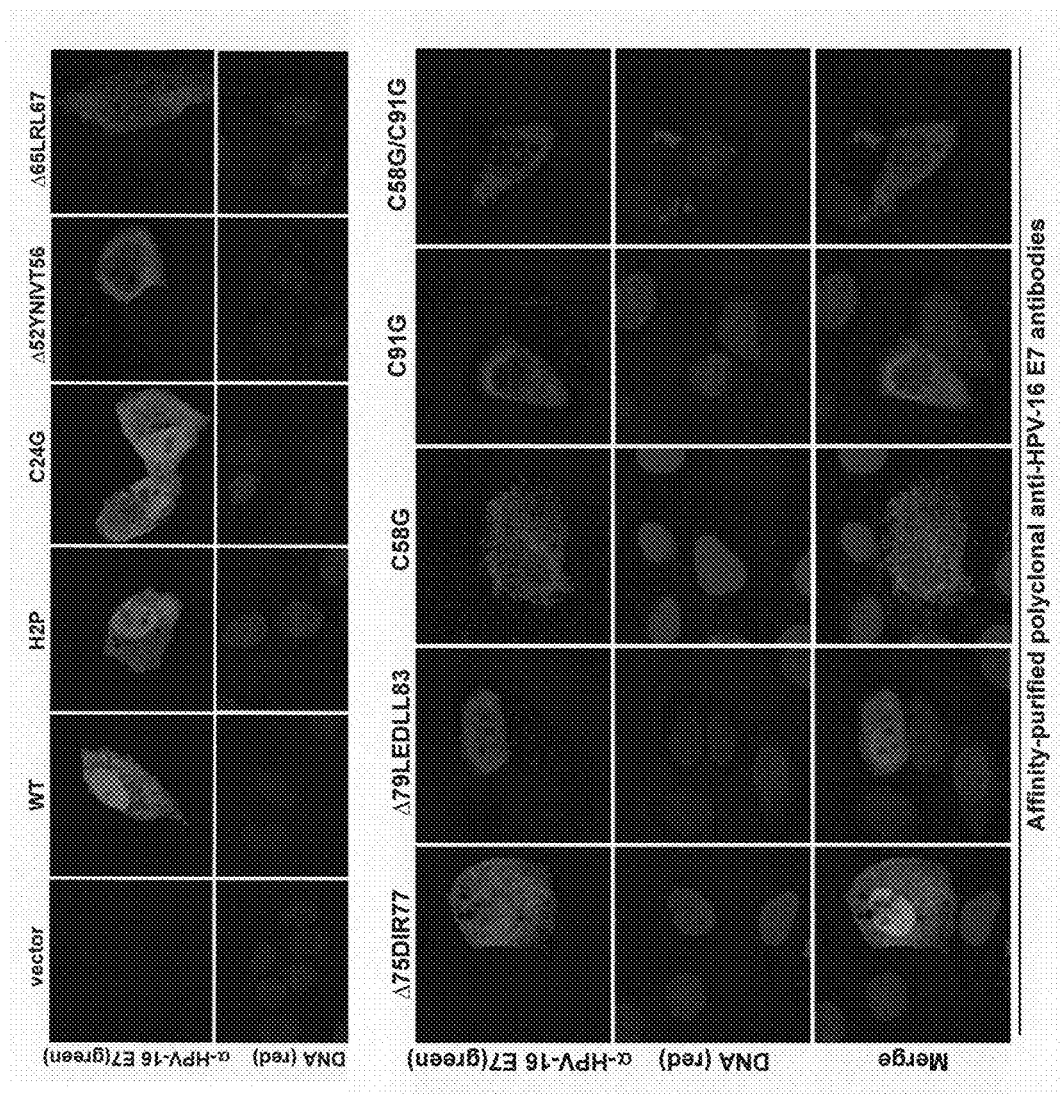

FIG. 8 A shows the detection of the wild-type and several mutated HPV 16 E7 proteins transiently expressed in U-2OS cells by the monoclonal antibody against HPV 16 E7 (2 ng/μl) followed by alexaFlour488-labelled secondary antibody in indirect immunofluorescence experiments. (vector=empty control vector, WT=wild-type). FIG. 8B shows the detection of the wild-type and mutated HPV 16 E7 protein, by known polyclonal anti HPV 16 E7 antibodies which do not specifically recognise the conformational epitope in the zinc finger domain and therefore also recognise the mutations concerning the cystein residues.

Figure 9:
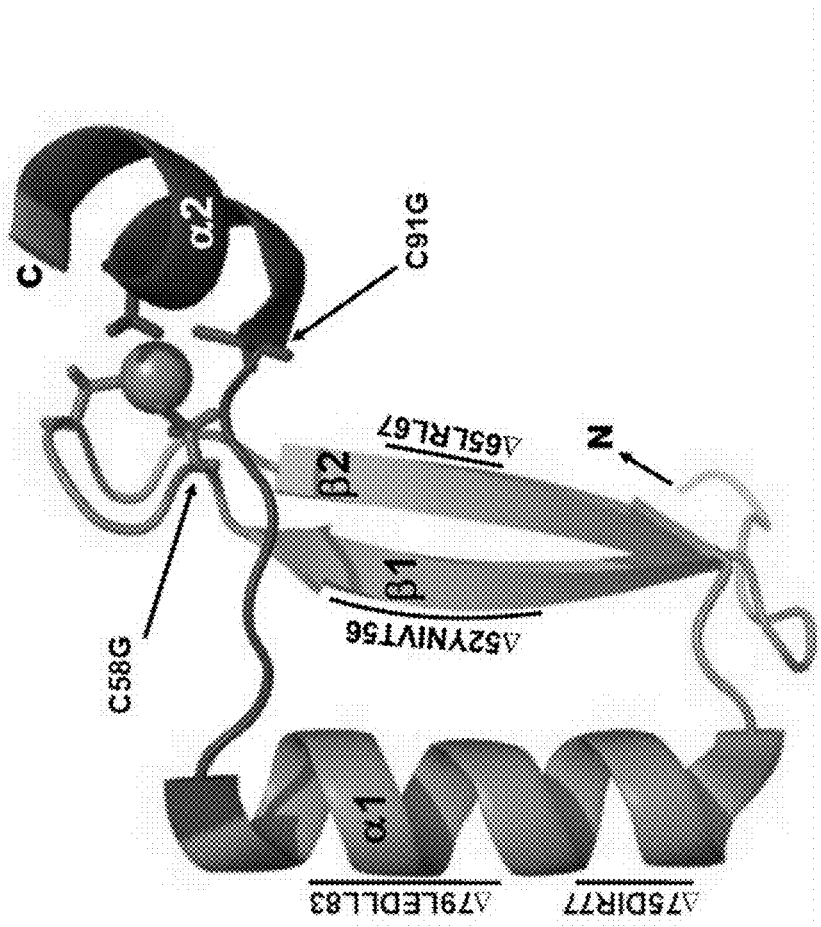

FIG. 9 shows a model of the structure of the HPV 16 E7 protein deduced from the NMR structure of HPV 45 E7, containing two β-sheets (β1 and β2) and two α-helices (α1 and α2) as secondary structures. The side chains of the four cysteins (C58, C61, C91, C94) in the two CXXC motifs coordinating zinc located in the turn connecting β1 and β2 and in the C-terminal α2-helix are indicated. The epitope 86TLGIVCPICSQK97 (SEQ ID No. 6) in the carboxyl-terminal E7 zinc-finger recognized by the monoclonal antibody is indicated. Moreover, the localization of the C-terminal mutations Δ52YNIVT56, Δ65LRL67, Δ75DIR77, Δ79LEDLL83, C58G and C91G are indicated. The unstructured N-terminus and the mutations H2P and C24G are not indicated.

Figure 10:
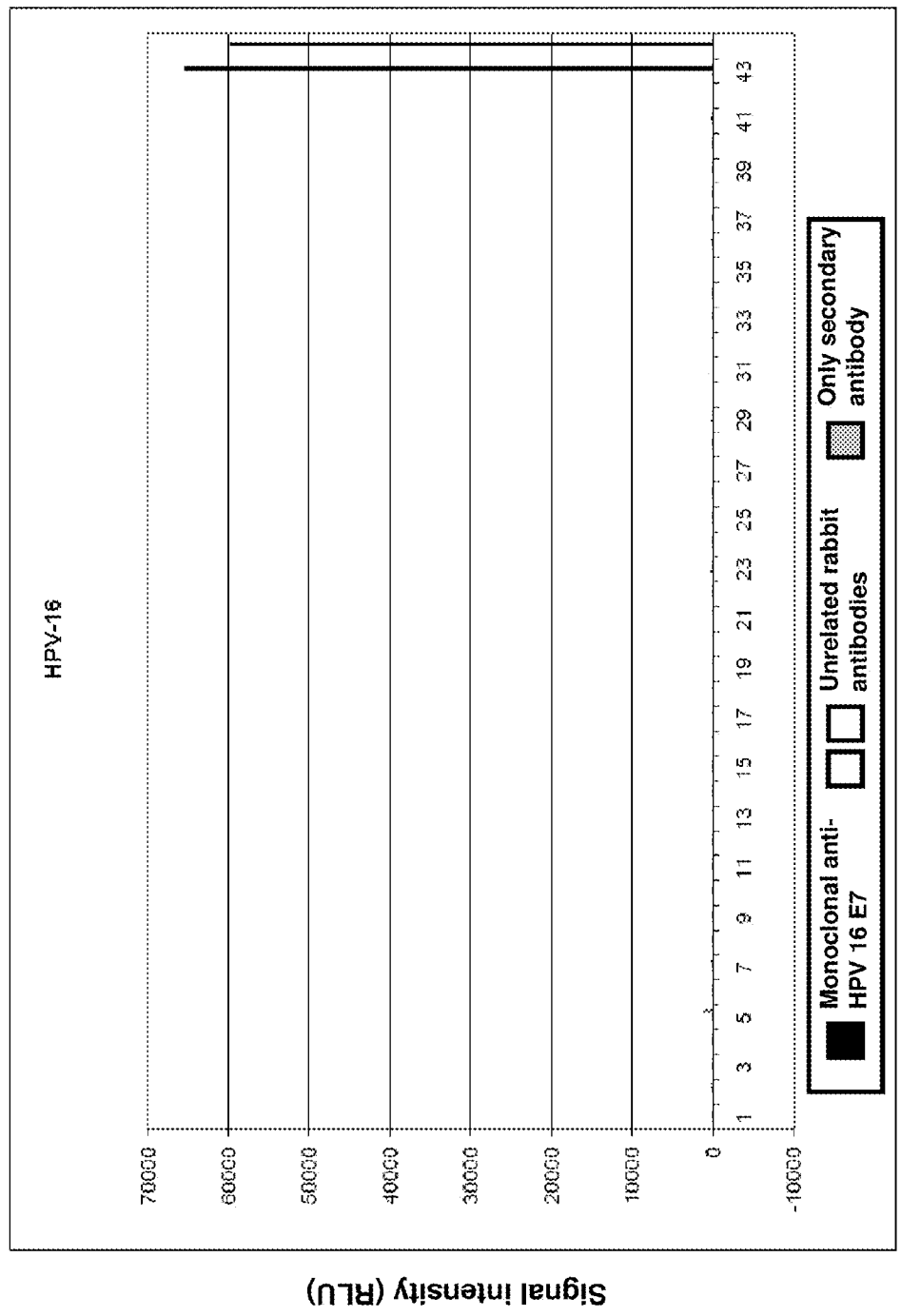

FIG. 10 shows epitope mapping using synthetic HPV 16 E7 13 mer peptides on microarrays which were detected by the monoclonal antibody against HPV 16 E7, two unrelated rabbit antibodies and the secondary antibody only (anti-rabbit Cy5). Specifically, peptides 43 and 44 are recognised by the monoclonal anti-HPV 16 E7 antibody which comprises the specific epitope.

Figure 11:
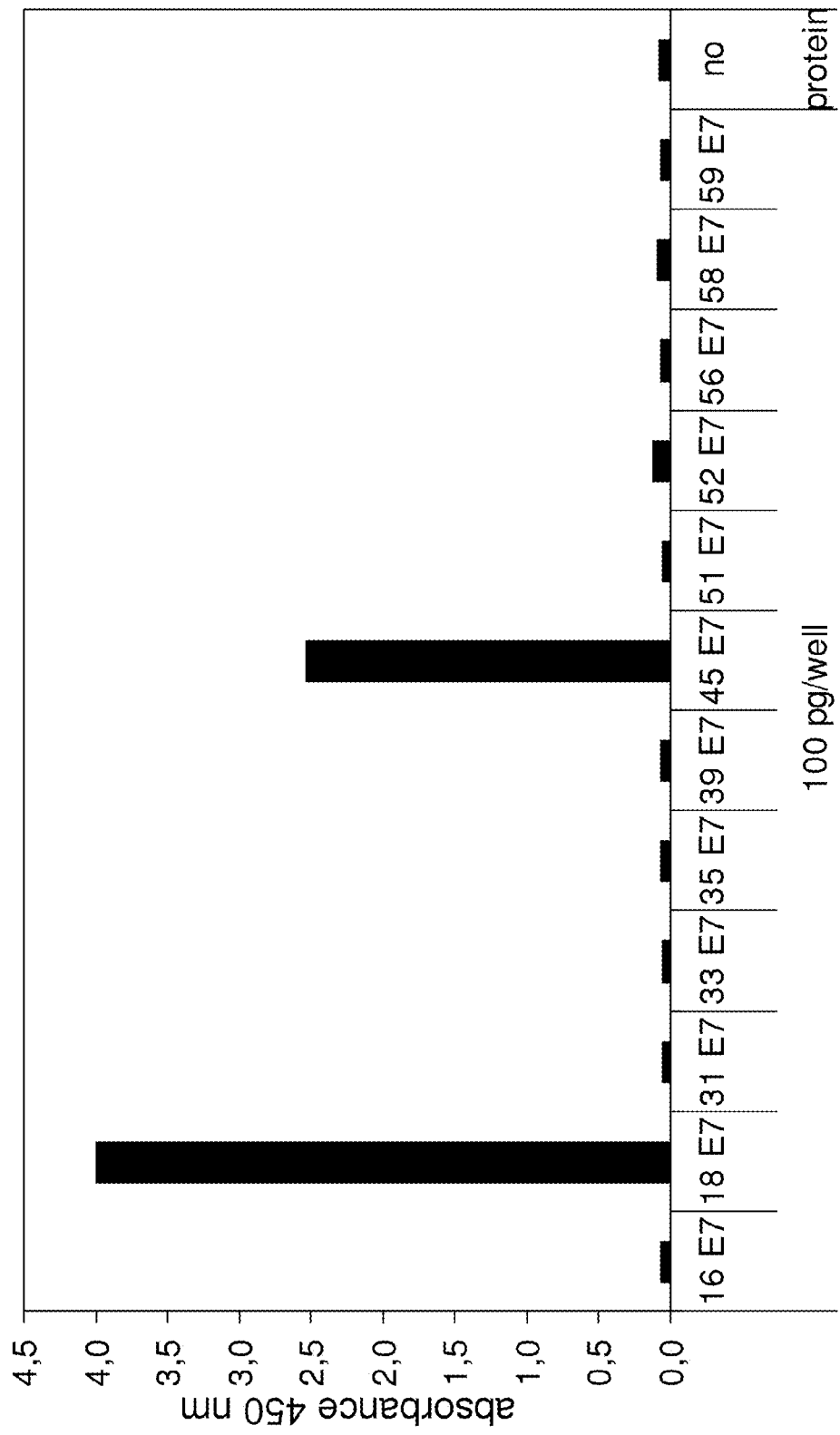

FIG. 11 shows the specificity of the monoclonal antibody against HPV 18 E7 employing an ELISA assay. ELISA plates were coated with a mixture (1:1) of goat polyclonal antibodies against HPV 16 E7 and HPV 18 E7. Then, 100 pg recombinant E7 protein of different HPV types was added. Subsequently, the biotinylated monoclonal anti-HPV 18 E7 antibody of the present invention was added for detection of the E7 proteins bound by the goat polyclonal antibodies, followed by incubation with Streptavidin-Poly-HRP-conjugate for visualization.

Figure 12:
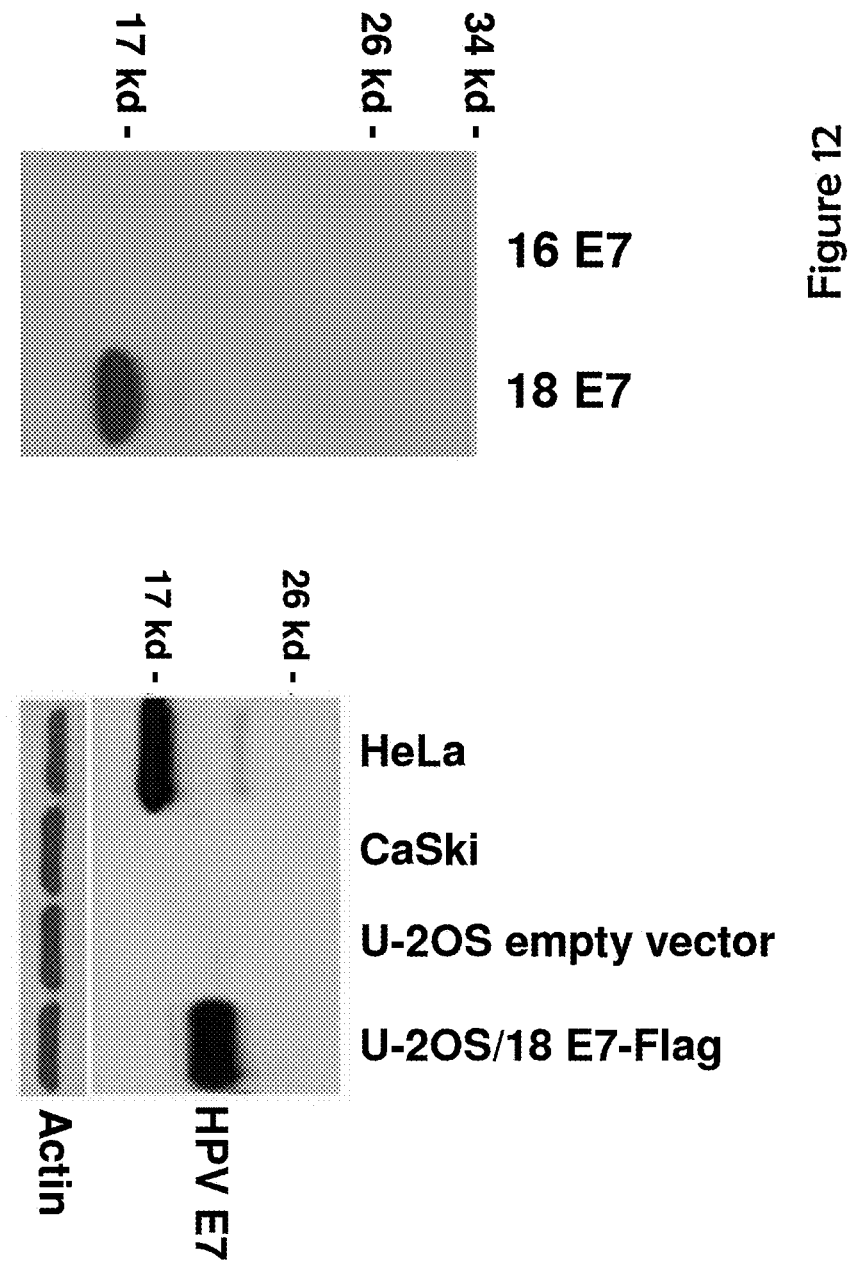

FIG. 12 shows a western blot with purified E7 protein of HPV 16 and 18 (10 ng) each loaded on a 12.5% SDS gel and probed with the antibody against HPV 18 E7, wherein only the HPV 18 E7 protein is recognized by the antibody (left panel) and cell extracts from HPV 18 positive HeLa cells, HPV 16 positive CaSki cells and U-2OS cells transfected either with an empty vector or an expression vector for HPV 18 E7. Cell lysates were separated by SDS-PAGE and probed in western blot with the antibody against HPV 18 E7 (right panel). Only the HPV 18 E7 protein is recognised by the antibody.

FIG. 13 shows epitope mapping using synthetic HPV 18 E7 11 mer peptides which were detected by the monoclonal antibody against HPV 18 E7, two unrelated rabbit antibodies and the secondary antibody only (anti-rabbit Cy5). Specifically, peptides 1 to 3 are recognised by the monoclonal anti-HPV 18 E7 antibody which comprise the specific epitope.

EXAMPLE 1

Generation and Purification of Rabbit Monoclonal Antibodies (RabMabs)

Purified HPV 16 and HPV 18 E7 proteins (purity>95%; 4 mg each) (Fiedler et al., J Gen Virol, 2005, 86, 3235-3241, and Fiedler et al., J Virol Methods, 2006, 134, 30-35) were used to immunize rabbits, and rabbit hybridoma clones were prepared. Selected hybridomas were taken in culture and supernatants (2 l each) were produced, which typically yielded 2 mg of the respective RabMab. Hybridoma supernatant was diluted with ⅓ binding buffer (20 mM sodium phosphate, pH 7) and filtered through a 0.45 µm filter. The column (HiTrap™ Protein G HP 5 ml; GE Healthcare) was washed with 5-10 column volumes of binding buffer at 5 ml/min. The filtered supernatant was applied and the column washed with 5-10 column volumes of binding buffer; eluted with 6×2 ml elution, buffer (0.1 M glycine-HCl, pH 2,7) into collection tubes with 80 µl 3 M Tris-HCl, pH 9. After elution, the column was washed with 5-10 column volumes of binding buffer followed by 5-10 column volumes of 20% ethanol. IgG-containing fractions were pooled and dialyzed overnight at 4° C. against dialysis buffer (166 mM potassium phosphate, 83 mM glycine, pH 7.2). After dialysis, samples were concentrated using concentration tubes (Amicon Ultra, MWCO 10,000 Millipore). Finally, the sample was cleared by centrifugation (13,000 rpm, 4° C., 10 min) and the IgG concentration was determined using OD at 280 nm. Aliquots were stored in liquid nitrogen.

Hybridoma clones producing the desired antibodies were selected after further testing and a hybridoma clone producing monoclonal anti-HPV 16 E7 antibodies has been deposited on 16$^{th}$ of Dec. 2009 with the DSMZ, Braunschweig, Germany, under the accession no. DSM ACC 3034 and a second hybridoma clone producing monoclonal anti-HPV 18 E7 antibodies has been deposited on 16$^{th}$ of Dec. 2009 with the DSMZ under the accession no. DSM ACC 3035.

EXAMPLE 2

Cross-Reactivity Test for E7 Antibodies

Overexpression in U-2OS Cells
U-2OS-cells (HPV negative) were transiently transfected with vectors for overexpression of selected E7 proteins. For confocal immunofluorescence microscopy, cells were fixed in 4% (w/v) PFA/PBS and permeabilized with 0.1% (w/v) sodium citrate/0.3% (v/v) TRITON™ X-100 t-octylphenoxypolyethoxyethanol. After blocking with 1% (w/v) bovine serum albumin/PBS, cells were incubated for 1 h with the monoclonal anti-HPV 16 E7 or anti-HPV 18 E7 of the present invention (25 µg/ml) at room temperature and analyzed by confocal microscopy.

The results showed that the anti-HPV 16 E7 antibody of the present invention did not cross-react with E7 proteins of other HPV types, such as HPV 18 and HPV 45, and the anti-HPV 18 E7 antibody of the present invention was able to detect E7 proteins of HPV 18 and 45, 11, 56, 58, 59 and 70.

Direct ELISA Assay
To more precisely characterise the cross reactivity of the monoclonal antibody against HPV 16 E7 an direct ELISA assay was used. Different amounts of randomly coated recombinant HPV E7 proteins of different HPV types were analysed regarding the reactivity of the monoclonal antibody against HPV 16 E7.

The assay was carried out as follows:
Wells of microtiter plates (Maxisorp F, Nunc, Vienna) were coated overnight (4° C.) with different amounts (2.5 and 10 ng) of recombinant bacterially produced untagged HPV E7 proteins in 100 µl of coating buffer (0.1 M NaHCO3, pH 9.6). After washing three times in PBS, pH 7.4, containing 0.05% TWEEN®20 polysorbate20, wells were blocked with 300 µl Universal Casein Diluent/Blocker (UCDB, SDT, Baesweiler, Germany) for 2 hours at room temperature. Wells were washed three times. 100 µl biotinylated primary monoclonal antibody against HPV 16 E7 (appropriate dilution in UCDB) was added to each well and incubated for 1 hour at room temperature. After three washing steps, 100 µl Streptavidin-PolyHRP40 conjugate (SDT, Baesweiler, Germany, 0.2 µl/ml in UCDB) were added to each well, followed by 1 hour incubation at room temperature. After washing six times, successful binding of the antibody was visualized by the addition of 100 µl chromogenic substrate (es(HS)TMB, SDT, Baesweiler, Germany) to each well and follow-up incubation for 30 min in the dark at room temperature. The reaction was stopped by the addition of 50 µl 2N H$_2$SO$_4$ and quantified by absorbance measurement (450 nm) in a multilabel plate reader (VICTOR™ X5, Perkin Elmer, Vienna, Austria).

As shown in FIG. 7, the monoclonal antibody against HPV 16 E7 very strongly detected the HPV 16 E7 protein, but did not cross react with all other HPV types, including ten other high-risk HPV genotypes and the two most common low-risk HPV viruses, HPV 6 and HPV 11.

ELISA Assay
To more precisely characterise the cross reactivity of the monoclonal antibody against HPV 18 E7 an ELISA assay was used (see example 5 for ELISA protocol). 100 pg of the respective recombinant HPV E7 proteins were added to the wells and detected with the anti-HPV 18 E7 antibody according to the present invention.

This experiment showed that the monoclonal anti-HPV 18 E7 antibody according to the present invention is highly specific for the E7 proteins of HPV 18 and 45 (see FIG. 11) but does not recognise the E7 proteins of other high-risk HPV types.

Western Blot
The specificity of the anti-HPV 18 E7 antibody of the present invention was also analyzed by Western blot. Purified recombinant E7 protein of the HPV types 16 and 18 was separated by SDS-PAGE and analyzed by Western blot using the anti-HPV 18 E7 antibody. No signal was obtained for recombinant E7 protein of HPV 16, whereas positive signals were obtained for recombinant HPV 18 E7 (FIG. 12). Similarly, specific signals were obtained with the anti-HPV 18 E7 antibody, when extracts of transiently transfected U-2OS cells, expressing FLAG-tagged versions of HPV 18 E7, were analyzed. Finally, endogenous E7 proteins of HPV 18 positive HeLa cells, but not of HPV-16 positive CaSki cells, were detectable by Western blot (FIG. 12).

EXAMPLE 3

Immunohistochemical Detection of HPV E7 Protein in Cervical Cancer Biopsies

To determine the HPV status in cervical biopsies from 30 patients, first, PCR analysis was used to determine the different HPV genotypes. 26 (87%) of the biopsies were HPV-DNA positive, nine (30%) contained only HPV 16 DNA and three (10%) only HPV 18 DNA. Eight (23%) were HPV 16 and 18 positive and six (23%) contained HPV 16, 18 and other HPV types. In the remaining four biopsies the HPV type was apparently not detectable by the PCR analysis. As negative controls, 22 cervical biopsies containing normal, squamous and glandular epithelia were used. To test, whether the anti-HPV 16 E7 and anti-HPV 18 E7 monoclonal rabbit antibodies according to the invention could detect the HPV E7 proteins in paraffin sections of these biopsies the following protocol for immunohistochemistry was employed.

Immunohistochemistry was performed on paraffin-embedded tissue sections derived from cervical biopsies. 2 μm sections were mounted on slides, deparaffinized in xylene (2×12 minutes), rehydrated and processed for antigen retrieval by treatment for 1 hour in a steamer in Target Retrieval Solution (DAKO S1700) for the detection of HPV E7. Endogenous peroxidase activity was blocked by incubation in 20% $H_2O_2$/methanol for 30 minutes. Sections were washed and incubated for minutes in blocking buffer (10% goat or rabbit serum from DAKOCytomation Germany, respectively, 5% BSA in 1×Tris buffer). Blocking solution was removed. The sections were either incubated with the biotinylated monoclonal rabbit anti-HPV 16 E7 or 18 E7 antibodies of the present invention (at appropriate dilutions) for 1 h at room temperature in 5% BSA/1×TBS in a wet chamber. Samples were rinsed in 1×Tris/0.1% TWEEN®20 polysorbate20 and incubated with secondary IgGs (DAKO-Cytomation, Germany) for 45 min at room temperature in a wet chamber. After washing, samples were incubated with streptavidin peroxidase conjugate (Sigma, Vienna) for 30 minutes at room temperature. Bound antibodies were visualized with DAB solution (Sigma, Vienna) as substrate. Counterstaining was performed with Hemalaun (Merck, Vienna). The specimens were dehydrated, and mounted using Entellan (Merck, Vienna). Brightfield microscopy with photography was performed using Olympus CH30 microscope and a Sony DSC-W15 Cyber-shot camera.

In all 23 biopsies tested positive for HPV 16 DNA by the PCR analysis, the anti-HPV 16 E7 antibody of the present invention recognised almost all epithelial tumor cells within the tumor islets but stained no cells in adjacent connective tissues. No HPV 16 E7 protein was detected in normal cervical specimens, neither in connective tissue and cervical glandular epithelia nor in normal cervical squamous epithelia.

To determine whether the HPV 18 E7 protein could be detected by the anti-HPV 18 E7 antibody of the present invention immunohistochemistry experiments were conducted using the biopsies tested positive for HPV 18 DNA by the PCR analysis. Similar to the anti-HPV 16 E7 antibody, the anti-HPV 18 E7 antibody stained almost all tumor cells within the respective tumors, but did not stain cells in the adjacent connective tissue. No staining was detected in normal cervical specimens.

Surprisingly, the anti-HPV 16 E7 as well as the anti-HPV 18 E7 antibody of the present invention could detect the respective protein in the four biopsies in which HPV DNA was undetectable by the PCR analysis, suggesting that the cells of these biopsies were indeed HPV infected which was not detected by the PCR analysis.

EXAMPLE 4

Detection of High-Risk HPV 16 E7 Proteins in Liquid-Based Cytology

Based on results obtained with paraffin sections, it was tested whether the anti-HPV 16 E7 antibody according to the present invention can be used in liquid-based cytology (LBC). To establish the procedure, LBC samples from healthy women were spiked with CaSki cells (HPV 16 positive), and U-205 cells (HPV negative) and processed according to the following protocol:

CaSki cells and U-2OS cells were harvested and resuspended in ThinPrep-Buffer (Cytyc SA, Geneva, Switzerland). Cervical swabs were resuspended in ThinPrep-Buffer, mixed with the cultured cells, and 10 to 100 μl of the mixture were dropped with a pipette on a ThinPrep-glass slide (Cytyc SA, Geneva, Switzerland). The cells were allowed to dry over night at room temperature. Cells were fixed using 4% PFA at RT for 30 min in a cuvette, and washed by gentle shaking 2×5 min at RT in TBS+0.05% TWEEN®20 polysorbate20. For antigen retrieval, cells were incubated with 10 mM NaCitrate pH 6.0+0.3% TRITON™ X-100 t-octylphenoxypolyethoxyethanol for 15 min at RT in a cuvette, washed 2×5 min at RT in TBS+0.05% TWEEN®20 polysorbate20. After peroxidase blocking, slides were incubated for 30 min with 200 μl normal goat serum (DakoCytomation) in a wet chamber (1:10 dilution in 1% BSA-TBS+0.05% TWEEN®20 polysorbate20). Each slide was incubated with 200 μl primary antibody at appropriate dilution in 1% BSA-TBS+0.05% TWEEN®20 polysorbate20 for 1 hour at RT in a wet chamber. Slides were washed and incubated with biotinylated secondary antibody (DakoCytomation) at appropriate dilution in 1% BSA-TBS+0,05% TWEEN®20 polysorbate20 for 1 hour at RT. Slides were washed and incubated with 200 μl Peroxidase Conjugate (Sigma; 1:500 dilution in 1% BSA-TBS+0.05% TWEEN®20 polysorbate20) in a wet chamber, and subsequently rinsed in distilled water. For visualization, peroxidase Substrate Kit SK-4200AEC-Kit (Vector, Vienna, Austria) was used. Haematoxylin served as counterstain.

This procedure yielded a very specific staining of the HPV 16 positive CaSki cells with the anti-HPV 16 E7 antibody of the present invention, whereas neither cervical cells from healthy probands, nor U-2OS cells were stained, suggesting a very high specificity of the antibody (see FIG. 6).

EXAMPLE 5

ELISA-Based HPV Diagnosis

Cell Lysis

Cells from cell cultures were washed with PBS and resuspended in ice-cold lysis buffer (PBS-0.1% TWEEN nonionic detergent TWEEN®20 polysorbate20, containing 1 complete EDTA-free protease inhibitor cocktail tablet (Roche) per 50 ml lysis buffer). Lysates were frozen at −80° C., thawed at room temperature, and centrifuged (4° C., 13,000 rpm, 20 min). Supernatants were processed in the ELISA procedure.

In the case of clinical samples, cervical smears were collected from the cervix using a brush. The brush was placed immediately into the collecting tube containing 1 ml lysis buffer without protease inhibitors (PBS-0.1% TWEEN®20 polysorbate20). After the stick of the brush was shortened and the collecting tube was closed, the sample was stored immediately at −80° C. until use. The sample was thawed at room temperature and immediately 20 μl of 50×protease inhibitor stock solution (complete EDTA-free, Roche) per collecting tube was added. After resuspending the remaining sample on the brush by mixing it in the lysis buffer, the remaining liquid from the brush was wiped off at the edge of the tube and the brush was discarded. The sample was centrifuged at 4° C., 13,000 rpm for 20 min. Supernatants were processed in the ELISA procedure.

ELISA Protocol

100 μl coating buffer (0.1 M NaHCO$_3$, pH 9.6) containing a mixture of goat polyclonal anti-high-risk HPV antibodies was added to each well of a 96 well plate (F96 Maxisorp Nunc-Immuno Plate), and incubated overnight at 4° C. Wells were washed 3× with washing buffer (PBS, 0.05% TWEEN®20 polysorbate20; pH 7.4); 300 μl blocking buffer (Universal Casein Diluent/Blocker, SDT) was added to each well, and incubated for 2 hours at room temperature. Wells were washed 3× with washing buffer, afterwards recombinant E7 protein or cell lysate (200 μl; diluted in lysis buffer: PBS, 0.1 TWEEN®20 polysorbate20, protease inhibitors) was added and incubated for 30 minutes at room temperature. Wells were aspirated and again 200 μl protein or cell lysate were added and incubated for 30 minutes at room temperature, Wells were washed 3× with washing buffer. 100 μl biotinylated monoclonal detection antibody (anti-HPV 16 E7 or anti-HPV 18 E7 antibodies of the present invention) in its appropriate dilution in Universal Casein Diluent/Blocker were added to each well, incubated for 1 hour at room temperature, and washed 3× with washing buffer. 100 μl SA-PolyHRP-conjugate (SDT) in its appropriate dilution in Universal Casein Diluent/Blocker were added to each well and incubated for 1 hour at room temperature. Afterwards wells were washed 6× with washing buffer. 100 μl detection reagent (es(HS)TMB, SDT) were added to each well, incubated for 30 min in the dark at room temperature. 50 μl stop solution (2N H$_2$SO$_4$) were added to each well, and absorbance (450 nm) determined by an ELISA reader.

Results

To determine the sensitivity of the monoclonal detection antibodies of the present invention decreasing amounts of the respective recombinant E7 protein were tested with the ELISA protocol. In this setting, 10 pg of HPV 16 E7 was easily detectable by the monoclonal anti-HPV 16 E7 antibody and similar sensitivity was obtained for the HPV 18 E7 antibody with HPV 18 E7 and HPV 45 E7 proteins (see FIG. 1).

When the monoclonal detection antibodies of the present invention were biotinylated and incubated with streptavidin-poly-HRP-conjugate instead of a secondary antibody, an additional signal amplification could be achieved. In this optimised setting, the specific detection limit of the monoclonal antibodies according to the present invention was reduced to 500 fg-1 pg in case of HPV 16 E7 and to 250 fg-500 fg for HPV 18 E7 protein (see FIG. 2).

With this setting it could also be shown that proteins of low-risk HPVs like HPV 6 or HPV 11 are not detected by the anti-HPV 16 E7 or the anti-HPV 18 E7 antibody of the present invention (see FIG. 3).

To determine, whether this ELISA format is suitable for the detection of E7 proteins in tumor cells, HPV negative cells (U-2OS) were mixed with decreasing amounts of HeLa cells (HPV 18 positive) and CaSki cells (HPV 16 positive), respectively. Cell mixtures were lysed and analyzed by ELISA (see above). These experiments reveealed that 2,500-5,000 CaSki cells as well as 500-1,000 HeLa cells (in the background of HPV negative U-2OS cells) can be detected by the respective antibody of the present invention (see FIG. 4).

To determine, whether E7 proteins could also be detected in clinical samples with this setting, cervical smears were tested. For this purpose, two consecutive Pap Smears were taken from patients or healthy probands. One sample was used for cytological classification according to Papanicolaou and subsequent determination of the HPV subtype by PCR analysis. The second sample was processed for the ELISA protocol (see above). In total, five samples were processed (one HPV 16 positive, one HPV 18 positive and three HPV negative), yielding clear signals above background using the antibodies according to the present invention for the HPV 16 and 18 positive samples, whereas the HPV negative samples did not produce a detectable signal. These data show that the sensitivity of the present assay employing the antibodies of the present invention is high enough to allow reliable detection of high-risk E7 proteins in clinical samples and thereby enabling reliable diagnosis of high-risk HPV infections (see FIG. 5).

EXAMPLE 6

Mutational Analysis of the Conformational Epitope Recognised by the Monoclonal Antibody Against HPV 16 E7

To further investigate the specificity of the monoclonal antibody against HPV 16 E7 to its epitope in the C-terminal domain U-2OS cells were transiently transfected with expression vectors for HPV 16 E7 mutants addressing the unstructured N-terminus as well as the major structure determining elements in the C-terminal domain. Preliminary western blot analysis showed that the protein levels of all HPV 16 E7 mutants were either similar or higher as the level of the HPV 16 E7 wild-type protein. To investigate whether the monoclonal anti HPV 16 E7 antibody is able to recognise the HPV 16 E7 mutants, an immunofluorescence assay was performed with the transiently transfected U-2OS cells. The analysed mutant HPV 16 E7 proteins were: H2P (change of histidine residue nr. 2 to proline), C24G (change of cysteine residue nr. 24 to glycine), deletions in the β1-sheet (Δ52YNIVT56), the β-sheet (Δ65LRL67), and the α1-helix (Δ75DIR77 and Δ79LEDLL83) as well as point mutations in the zinc coordination site of the zinc finger domain (C58G, C91G and C58G/C91G). The positions of the mutations within the HPV 16 E7 protein are also indicated in FIG. 9.

As shown in FIG. 8 A the monoclonal antibody against HPV 16 E7 recognised all deletion mutants, but was not able to recognise the point mutations concerning the cystein residues of the zinc coordination site. This indicates that the recognised epitope is located in the zinc finger structure and, more importantly, an intact zinc finger domain, which can not be formed if one or more of the cystein residues is mutated, is necessary for the efficient recognition of the HPV 16 E7 protein by the monoclonal anti HPV 16 E7 antibody. In contrast, as shown in FIG. 8B, known polyclonal antibodies against HPV 16 E7 which do not recognise the specific conformational epitope recognised by the monoclonal antibody against HPV 16 E7 also can detect the mutations concerning the cystein residues of the zinc finger domain.

For the indirect immunofluorescence experiments the following protocol was used:

Cells were fixed with 4% (w/v) PFA/1×PBS, permeabilized with 0.1% (w/v) Na-Citrate/0.3% (v/v) TRITON™ X-100 t-octylphenoxypolyethyoxyethanol, blocked with 1×PBS/1% BSA and incubated for 1 hour at 37° C. with the anti HPV 16 E7 antibody in 1×PBS/1% BSA. After washing in 1×PBS and staining with alexaFlour488-labelled secondary antibody (DAKOCytomation, Hamburg), cells were processed for indirect immunofluorescence microscopy and viewed using a confocal laser-scanning system.

EXAMPLE 7

Epitope Mapping

HPV 16 E7 epitopes were analyzed by JPT Peptide Technologies GmbH (Berlin, Germany) using peptide microarrays. To do this, a collection of 44 different HPV 16 E7 derived 13mer peptides, positioned on peptide microarrays, were incubated with the monoclonal antibody against HPV 16 E7 and unrelated rabbit control antibodies. The determination of peptide-antibody binding was performed by Repli-Tope-analysis where the peptide microarray was incubated with the primary antibody followed by a fluorescently labelled secondary antibody (anti-rabbit-Cy5). After washing the peptide microarrays were dried using a microarray centrifuge and scanned in a high resolution microarray scanning system with appropriate wavelength settings.

As shown in FIG. 10, peptides 43 and 44 which comprise amino acids 85 to 97 (SEQ ID No. 3) and 86 to 98 (SEQ ID No. 7), respectively, are specifically recognised by the monoclonal antibody against HPV 16 E7, indicating that these amino acids represent the recognised epitope.

Similarly, a collection of 47 different HPV 18 E7 derived overlapping 11mer peptides was used for epitope mapping for the anti-HPV 18 E7 antibody according to the present invention. The peptide microarrays were incubated with the anti-HPV 18 E7 antibody as well as two unrelated monoclonal antibodies.

As shown in FIG. 13, peptides 1 to 3 which comprise the N-terminal amino acids 4 to 13 of the HPV 18 E7 protein are specifically recognized by the anti-HPV 18 E7 antibody of the present invention.

---

The invention claimed is:

1. A hybridoma cell line deposited as Klon 42-3-78 at the Leibniz Institute DSMZ-German Collection of Microorganisms and Cell Cultures on Dec. 16, 2009 with accession no. DSM ACC3034 or deposited as Klon 143-7-33 at the Leibniz Institute DSMZ-German Collection of Microorganisms and Cell Cultures on Dec. 16, 2009 with accession no. DSM ACC3035.

2. A monoclonal anti-HPV E7 antibody obtained from the hybridoma cell line of claim 1.

3. The monoclonal anti-HPV E7 antibody according to claim 2, wherein the antibody is labelled with a radioactive, enzymatic or fluorescent group.

4. The monoclonal anti-HPV E7 antibody according to claim 2, wherein the monoclonal anti-HPV E7 antibody is capable of specifically recognizing an epitope of the C-terminal region of an HPV E7 protein, wherein the epitope comprises the amino acid sequence set forth in SEQ ID No. 3, 6, or 7.

5. The monoclonal anti-HPV E7 antibody according to claim 2, wherein the monoclonal anti-HPV E7 antibody is capable of specifically recognizing an epitope of the N-terminal region of an HPV E7 protein, wherein the epitope comprises the amino acid sequence set forth in SEQ ID No. 5 or 8.

6. The monoclonal anti-HPV E7 antibody according to claim 2, wherein the monoclonal anti-HPV E7 antibody detects native, non-denatured HPV E7 proteins.

7. An in vitro method for detection of human papillomavirus (HPV) E7 protein from HPV 16 and HPV 18, the method comprising:
   i) incubating a biological sample with a monoclonal anti-HPV E7 antibody capable of specifically recognizing an HPV 16 subtype or HPV 18 E7 protein the monoclonal anti-HPV E7 antibody being derived from the hybridoma cell line deposited as Klon 42-3-78 at the Leibniz Institute DSMZ-German Collection of Microorganisms and Cell Cultures on Dec. 16, 2009 with accession no. DSM ACC3034 or from the hybridoma cell line deposited as Klon 143-7-33 at the Leibniz Institute DSMZ-German Collection of Microorganisms and Cell Cultures on Dec. 16, 2009 with accession no. DSM ACC3035; and
   ii) measuring and/or detecting HPV E7 protein in the biological sample by measuring and/or detecting the antibody specifically bound to the E7 protein.

8. The method according to claim 7, wherein the monoclonal antibody is a monoclonal anti-HPV E7 antibody capable of specifically recognizing an epitope of the C-terminal region of an HPV E7 protein, wherein the epitope comprises the amino acid sequence set forth in SEQ ID No. 3, 6, or 7.

9. The method according to claim 8, wherein the epitope is an epitope of a zinc finger domain of the C-terminal region of the HPV E7 protein.

10. The method according to claim 8, wherein the epitope is a conformational epitope.

11. The method according to claim 7, wherein the monoclonal antibody is a monoclonal anti-HPV E7 antibody capable of specifically recognising an epitope of the N-terminal region of an HPV E7 protein, wherein the epitope comprises the amino acid sequence set forth in SEQ ID No. 5 or 8.

12. The method according to claim 11, wherein said antibody is labelled with a radioactive, enzymatic or fluorescent group.

13. The method according to claim 7, wherein the E7 protein is the E7 protein of HPV 45.

14. The method of claim 8, wherein said antibody is labelled with a radioactive, enzymatic or fluorescent group.

15. The method according to claim 7,
   wherein measuring and/or detecting HPV E7 protein in the biological sample includes detecting HPV 16 or HPV 18 E7 protein in the biological sample by detecting the antibody specifically bound to the HPV 16 or HPV 18 E7 protein and thereby allowing a diagnosis of a HPV infection.

16. The method of claim 15, wherein the monoclonal antibody is a monoclonal anti-HPV E7 antibody capable of specifically recognizing an epitope of the C-terminal region of an HPV E7 protein, wherein the epitope comprises the amino acid sequence set forth in SEQ ID No. 3, 6, or 7.

17. The method of claim 15, wherein the monoclonal antibody is a monoclonal anti-HPV E7 antibody capable of specifically recognising an epitope of the N-terminal region of an HPV E7 protein, wherein the epitope comprises the amino acid sequence set forth in SEQ ID No. 5 or 8.

18. An in vitro method for ELISA-based diagnosis of human papillomavirus (HPV) infections, the method comprising:
   a) coating a support with capture antibodies directed against HPV 16 or HPV 18 E7 proteins,
   b) adding a biological sample to the coated support,
   c) incubating the support with a monoclonal anti-HPV E7 detection antibody capable of specifically recognizing an HPV 16 subtype or HPV 18 E7 protein the monoclonal anti-HPV E7 antibody being derived from the hybridoma cell line deposited as Klon 42-3-78 at the Leibniz Institute DSMZ-German Collection of Microorganisms and Cell Cultures on Dec. 16, 2009 with accession no. DSM ACC3034 or from the hybridoma cell line deposited as Klon 143-7-33 at the Leibniz Institute DSMZ-German Collection of Microorganisms and Cell Cultures on Dec. 16, 2009 with accession no. DSM ACC3035, and
   d) identifying HPV 16 or HPV 18 E7 protein specifically bound by the capture antibodies by detecting the monoclonal detection antibody specifically bound to the HPV 16 or HPV 18 E7 protein and thereby allowing diagnosis of a HPV infection.

19. The method according to claim 18, wherein the monoclonal antibody is a monoclonal anti-HPV E7 antibody capable of specifically recognizing an epitope of the C-terminal region of an HPV E7 protein, wherein the epitope comprises the amino acid sequence set forth in SEQ ID No. 3, 6, or 7.

20. The method according to claim 18, wherein the monoclonal antibody is a monoclonal anti-HPV E7 antibody capable of specifically recognising an epitope of the N-terminal region of an HPV E7 protein, wherein the epitope comprises the amino acid sequence set forth in SEQ ID No. 5 or 8.

21. An in vitro method for ELISA-based diagnosis of human papillomavirus (HPV) infections, the method comprising:
   a) coating a support with a monoclonal anti-HPV E7 capture antibody derived from the hybridoma cell line deposited as Klon 42-3-78 at the Leibniz Institute DSMZ-German Collection of Microorganisms and Cell Cultures on Dec. 16, 2009 with accession no. DSM ACC3034 or from the hybridoma cell line deposited as Klon 143-7-33 at the Leibniz Institute DSMZ-German Collection of Microorganisms and Cell Cultures on Dec. 16, 2009 with accession no. DSM ACC3035,
   b) adding a biological sample to the coated support,
   c) incubating the support with detection antibodies directed against HPV 16 or HPV 18 E7 proteins, and
   d) identifying HPV 16 or HPV 18 E7 protein specifically bound by the monoclonal capture antibody by detecting detection antibodies specifically bound to the E7 protein and thereby allowing diagnosis of a HPV infection.

22. The method of claim 21, wherein the monoclonal anti-HPV E7 capture antibody is specifically capable of specifically recognizing an epitope of the C-terminal region of HPV 16 E7 or an epitope of the N-terminal region of HPV 18 E7 or HPV 45 E7.

* * * * *